(12) United States Patent
Mori et al.

(10) Patent No.: US 6,849,724 B1
(45) Date of Patent: Feb. 1, 2005

(54) METHOD FOR TRANSFORMING PLANT, THE RESULTANT PLANT AND GENE THEREOF

(75) Inventors: Satoshi Mori, Narashino (JP); Hiromi Nakanishi, Tokyo (JP); Hiroyuki Oki, Tokyo (JP); Hirotaka Yamaguchi, Tokyo (JP)

(73) Assignee: Japan Science and Technology Corporation, Saitama-Ken (JP)

( * ) Notice: Subject to any disclaimer, the term of this patent is extended or adjusted under 35 U.S.C. 154(b) by 0 days.

(21) Appl. No.: 09/646,825

(22) PCT Filed: Mar. 24, 1999

(86) PCT No.: PCT/JP99/01481

§ 371 (c)(1),
(2), (4) Date: Sep. 22, 2000

(87) PCT Pub. No.: WO99/48356

PCT Pub. Date: Sep. 30, 1999

(30) Foreign Application Priority Data

Mar. 24, 1998 (JP) .......................................... 10-096637

(51) Int. Cl.[7] .......................... C07H 21/04; C12N 15/00
(52) U.S. Cl. .................... 536/23.1; 536/23.2; 536/24.1; 536/23.6; 536/24.3
(58) Field of Search .............................. 536/23.1, 23.2, 536/24.1, 24.3, 23.6

(56) References Cited

FOREIGN PATENT DOCUMENTS

EP          0 385 962 A      9/1990

OTHER PUBLICATIONS

Wilson et al., Biochemical and Biophysical Research communications, vol. 232, pp. 678–681, 1997.*
James A. Wells, Additivity of Mutational Effects in Proteins, Biochemistry, vol. 29, No. 37, Sep. 18, 1990, pp. 8509–8517.*
J. Thomas Ngo et al., Computational Complexity, Protein Structure Prediction, and the Levinthal Paradox, pp. 492–495, 1994.*
Peer Bork, Powers and Pitfalls in Sequence Analysis: The 70% Hurdle, Genome Research, pp. 398–400, vol. 10, 2000.*
Jeffrey Skolnick et al., Trends in Biotech, 18(1): 2000, pp. 34–39.*
Doerks et al. TIG, Jun. 1998, vol. 14, No. 6, pp. 248–250.*
Temple F. Smith, Nature Biotechnology, vol. 15, Nov., 1997, pp. 1222–1223.*
Steven E. Brenner, TIG, Apr., 1999, vol. 15, No. 4, pp. 132–133.*
Boork et al. TIG, Oct., 1996, vol. 12, No. 10, pp. 425–427.*
Rothnie, Helen M., "Plant mRNA 3' –end formation.", Plant Molecular Biology, vol. 32, No. 1–2, 43–61 (1996).

Li Qingshun et al., "The polyadenylation of RNA in plants.", Plant Physiology (Rockville), vol. 115, No. 2, 321–325 (1997).
Van Der Salm, Theo et al., "Insect resistance of transgenic plants that express modified Bacillus thuringiensis cryIA(b) and cryIC genes: A resistance management strategy.", Plant Molecular Biology, vol. 26, No. 1,. 51–59 (1994).
Diehn, Scott H. et al., "Premature polyadenylation at multiple sites within a Bacillus thuringiensis toxin gene–coding region.", Plant Physiology (Rockville), vol. 117, No. 4. 1433–1443 (1998).
Oki Hiroyuki et al., "Introduction of the reconstructed yeast ferric reductase gene, refre1, into tobacco.", Plant and Soil, vol. 215, No. 2, 211–220 (1999).
Fujimoto et al., "Insect Resistant Rice Generated by Introduction of a Modified δ–endotoxin Gene of Bacillus thuringiensis", *Bio/Technology*, vol. 11, pp. 1151–1155 (1993).
Perlak et al., "Modification of the coding sequence enhances plant expression of insect control protein genes", *Proc. Natl. Acad. Sci. USA*, vol. 88, pp. 3324–3328 (1991).
Iannacone et al., "Specific sequence modifications of a cry3B endotoxin gene result in high levels of expression and insect resistance", *Plant Mol. Biol.*, vol. 34, pp. 485–496 (1997).
Pamela J. Green, "Control of mRNA Stability in Higher Plants"*Plant Physiol.*, vol. 102, pp. 1065–1070 (1993).
Dancis et al., "Ferric reductase of Saccharomyces cerevisiae: Molecular characterization, role in iron uptake, and transcriptional control by iron", vol. 89, pp. 3869–3873 (1992).
Johnston et al., "The nucleotide sequence of Saccharomyces cerevisiae chromosome XII", *Nature*, vol. 387 (6632 Suppl), pp. 87–90 (1997).
Keith et al., "Monocot and dicot pre–mRNAs are processed with different efficiencies in transgenic tobacco", *The EMBO Journal*, vol. 5, pp. 2419–2425 (1986).

* cited by examiner

*Primary Examiner*—Sean McGarry
(74) *Attorney, Agent, or Firm*—Peter F. Corless; Christine C. O'Day; Edwards & Angell, LLP

(57) ABSTRACT

A method for achieving the sufficient expression of a gene in a useful higher plant which has been transformed by transferring the above gene encoding a protein having a function carried by another organism so as to impart the function to the plant. Namely, a method for transforming a useful plant by transferring a gene of another species into the plant characterized in that the region of a factor relating to the poly(A) addition of the mRNA of the useful plant to be transformed contained in the base sequence of the gene of the other species is denatured into another base sequence not relating to the poly(A) addition of the mRNA without substantially altering the function of the protein encoded by the gene to be transferred; and a gene usable in the gene transfer.

2 Claims, 19 Drawing Sheets

Two Kinds of Fe-Uptake Mechanisms in Higher Plants

```
Seq 37
           putative poly(A)                              putative poly(A)
           poly(A) signal     site                       poly(A) signal    site
541  TCCGTC AAAAAT CACTTATTT ATCCTTCTGTTACAAAGATTAAT GAA CTTTTT ATTTATGGAAGCGTCTACCATTTAATTTT  630
181     S  V  K  K  S  L  I  Y  P  S  V  V  Y  K  D  Y  N  E  R  T  F  F  Y  L  W  K  R  L  P  F  N  F      210 putative                 poly(A) poly(A)
                              poly(A) signal           site    site
631  ACAACTCGAGGCAAGGGTCTCTGCTCGTCG TATTAA TTTTTGTT ATTTGACT ATATTATTCCTCAGTTTTGGTCATAATATTAAACTTCCACAC  720
211     T  T  R  G  K  G  L  V  V  L  I  F  V  I  L  T  I  L  S  F  G  H  N  I  K  L  P  H      240
```

FIG. 3

| 1 | ATGGTTAGAACCCGTGTATTATTCTGGTTATTTATATCTTTTTTTGCTACGGTTCAATCG | 60 |
| 61 | AGTGCTAGACTTATTAGCACTTCATGTATTTCCCAAGCTGCGCTATACCAATTTGGATGT | 120 |
| 121 | TCTAGTAAATCTAAAAGTTGCTACTGTAAAAACATCAATTGGCTGGGTTCAGTGACAGCA | 180 |
| 181 | TGTGCCTATGAGAATTCCAAATCTAACAAAACACTAGACAGCGCCTTAATGAAGTTAGCA | 240 |
| 241 | TCCCAATGTTCAAGCATCAAAGTTTATACTTTAGAGGACATGAAGAATATTTATTTAAAT | 300 |
| 301 | GCGTCAAATTATTTGAGAGCACCTGAGAAAAGTGATAAAAAAACCGTGGTTAGTCAACCG | 360 |
| 361 | CTCATGGCGAACGAGACAGCGTATCATTATTATTATGAGGAAAATTATGGTATCCATCTT | 420 |
| 421 | AACCTAATGCGCTCTCAATGGTGGGGTTGGGGTGTGGTGTTCTTGTGGGTGGGTGTGGTT | 480 |
| 481 | ACTGCAGCCACTATCTTGAACATTCTGAAAAGGGTGTTTGGTAAGAACATCATGGCAAAC | 540 |
| 541 | TCCGTCAAAAAATCACTTATTTATCCTTCTGTTTACAAAGATTATAATGAACGAACTTTT | 600 |
| 601 | TATTTATGGAAGCGTCTACCATTTAATTTTACAACTCGAGGCAAGGGTCTCGTCGTATTA | 660 |
| 661 | ATTTTTGTTATTTTGACTATATTATCTCTCAGTTTTGGTCATAATATTAAACTTCCACAC | 720 |
| 721 | CCATATGATAGGCCCAGATGGAGAAGAAGTATGGCCTTTGTGAGTCGTAGAGCAGACTTG | 780 |
| 781 | ATGGCCATTGCACTTTTCCCAGTAGTCTATCTATTCGGAATAAGAAATAATCCCTTCATC | 840 |
| 841 | CCTATAACAGGGCTTTCCTTTTCTACATTTAATTTCTATCATAAATGGTCTGCCTACGTT | 900 |
| 901 | TGTTTCATGTTGGCCGTTGTACACTCAATTGTCATGACCGCCTCGGGAGTGAAAAGAGGT | 960 |
| 961 | GTGTTTCAAAGTCTGGTTAGGAAATTTTACTTTAGGTGGGGTATAGTGGCAACGATATTA | 1020 |
| 1021 | ATGTCTATTATTATTTTCCAAAGTGAAAAAGTATTTAGAAATAGAGGGTATGAGATATTC | 1080 |
| 1081 | CTTCTTATTCATAAAGCGATGAATATTATGTTCATTATTGCCATGTACTACCATTGTCAC | 1140 |
| 1141 | ACCCTGGGCTGGATGGGTTGGATTTGGTCAATGGCTGGTATTTTATGCTTTGATAGATTC | 1200 |
| 1201 | TGCAGGATTGTTAGAATAATCATGAATGGTGGCTTGAAAACTGCTACTTTGAGTACCACT | 1260 |
| 1261 | GATGATTCTAATGTTATTAAATTTCAGTAAAAAAACCAAAGTTTTTCAAGTACCAAGTA | 1320 |
| 1321 | GGAGCTTTCGCATACATGTATTTCTTATCACCAAAAAGTGCATGGTTCTATAGTTTCCAA | 1380 |
| 1381 | TCACATCCATTTACAGTATTATCGGAACGACACCGTGATCCAAACAATCCAGATCAATTG | 1440 |
| 1441 | ACGATGTACGTAAAGGCAAATAAAGGTATCACTCGAGTTTTGTTATCGAAAGTTCTAAGT | 1500 |
| 1501 | GCTCCAAATCATACTGTTGATTGTAAAATATTCCTTGAAGGCCCATATGGTGTAACGGTT | 1560 |
| 1561 | CCACATATCGCTAAGCTAAAAAGAAATCTGGTAGGTGTAGCCGCTGGTTTGGGTGTTGCG | 1620 |
| 1621 | GCTATTTATCCGCACTTTGTCGAATGTTTACGGTTACCATCTACTGATCAACTTCAGCAT | 1620 |
| 1681 | AAATTTTACTGGATTGTTAATGACCTATCCCATTTGAAATGGTTTGAAAATGAATTGCAA | 1740 |
| 1741 | TGGTTAAAGGAGAAAAGTTGTGAAGTCTCAGTCATATATACTGGTTCCAGTGTTGAGGAC | 1800 |
| 1801 | ACAAATTCAGATGAGAGTACAAAAGGTTTTGATGATAAAGAAGAAAGCGAAATCACTGTT | 1860 |
| 1861 | GAATGTCTCAATAAAAGACCTGATTTGAAAGAACTAGTGCGCTCGGAAATAAAACTCTCA | 1920 |
| 1921 | GAACTAGAGAATAATAATATTACCTTTTATTCCTGCGGGCCAGCAACGTTTAACGACGAT | 1980 |
| 1981 | TTTAGAAATGCAGTGGTCCAAGGTATAGACTCTTCCTTGAAGATTGACGTTGAACTAGAA | 2040 |
| 2041 | GAAGAAAGTTTTACATGGT | 2059 |

FIG. 4

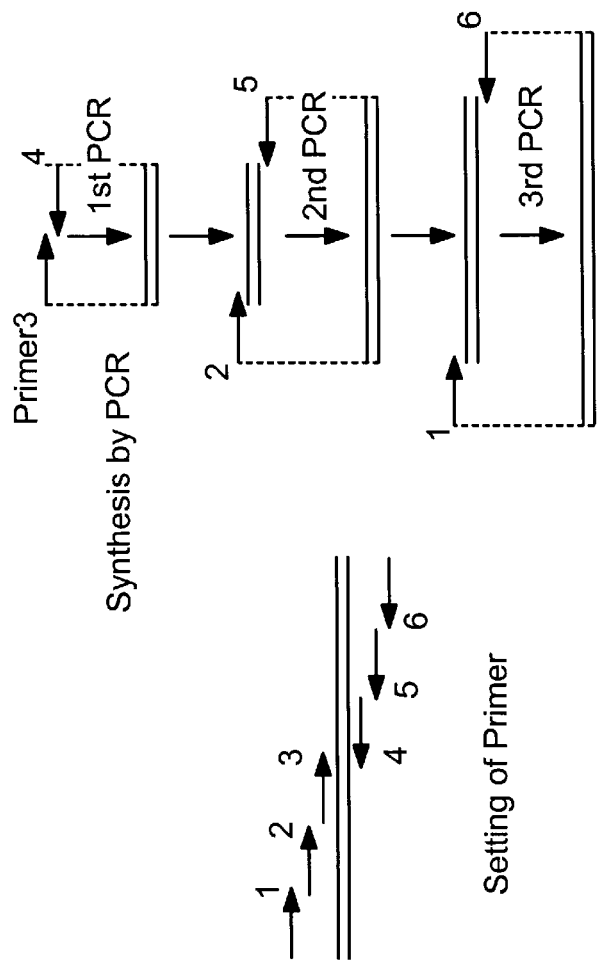
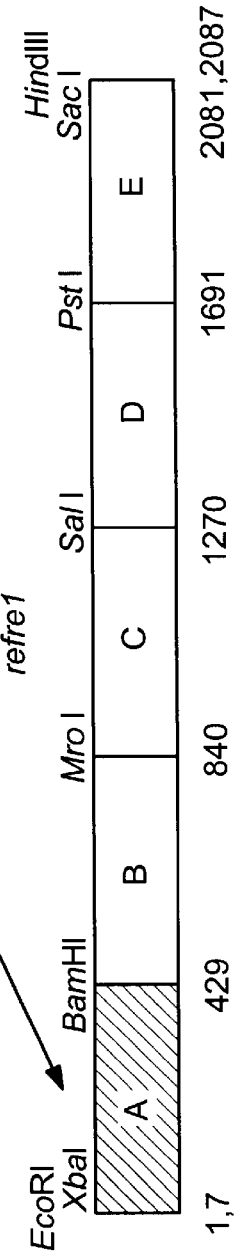
FIG. 5

FIG. 6

| | FIG. 6A |
|---|---|
| | FIG. 6B |

FIG. 6A

| Sequence Name | Base Sequence | |
|---|---|---|
| | 5'  →  3' | |
| A-1 | GAATTCTCTAGACTCCACCATGGTTAGAACCAGAGTCCTTTTCGCCTCTTCATCTCTTTTCGCCTACAGTCCAATCGAGCG | 83mer |
| A-2 | GTCCAATCGAGCGCTACACTACTTCCATCTCATGCATTTCAGGCTGCACTGTACCAGTTCGGATGCTCAAGCAAGTCAAA | 83mer |
| A-3 | CAAGCAAGTCAAAGTCTTGCTACTGCAAGAACATCAATTGGCTCCGAAGCGTCACTGCCTTATCGAGAACTCCAAATCT | 83mer |
| A-4 | TCCAGTGTGTAAACCTTGATACTTGAGCATTGGCTGGCCAAGTTCATCAAAGCGGAGTCCAGAGTCTCTTGTTAGATTTGAGTT | 83mer |
| A-5 | TGTCTTCTTATCGGATTTCTCAGGAGCGCCGAAGGTAGTTACTTGCATTAAGGTAGAATGTTCTTCATGTCCTCCAGTGTGTAAA | 83mer |
| A-6 | GGATCCCATAGTTTTTCCTATAGTAGTAGATAGCCGTCTCATTTGCCATCAACGGTTGTGAAACAACTGTCTTCTTATCG | 83mer |
| B-1 | GGATCCACTTGAATTTGATGCGATCTCAATGGTGCCGATCTCAATGGTGCGCATGGGCCCTCGTCTTCTTCTGGGTCGAGTCCTTACCGGCGCA | 80mer |
| B-2 | CCTTACCGCCGCAACTATCTTGAACATTCTCAAACGCGTATTCGGCAAGAACATTATGGCAAATTCTGTTAAGAAGTCTC | 80mer |
| B-3 | GTTAAGAAGTCTCTTATCTACCCAAGCGTTACAAAGACTACAGAGAACTACAGAGTCCTTTGCCTCGAGTTGTAAAGTTGAATGGCAAACGT | 80mer |
| B-4 | AGAGTGAGAGAATAGTCAGAATGACAAAGATAAGAACTACGAGTCCTTTGCCTCGAGTTGTAAAGTTGAATGCAAACGT | 80mer |
| B-5 | AATGCCATTGATCTTCCATCTAGTCTATCGTAAGGATGTGGCAACTTGATGTTATGTCCGAAAGAGAGTGAGAAT | 80mer |
| B-6 | TCCGGATACCGAAAAGTACACCACGGGGAAAAGAGCCATTGCCATCAAGTCAAGTCAAGTCAAGCGGCGTGAGACGAATGCCATTGAT | 80mer |
| C-1 | TCCGGAACAACCCCTTCATCCCAATCACCGGATTGAGCTTTAGTACTTTCAACTTTTACCACAAATGGTCAGCATACGTCTGC | 83mer |
| C-2 | GCATACGTCTGCTTCATGTTAGCCGTCGTGCTTCATTCAATCGTTATGACCGCTTCAGGAGTTAAACCGCTTAAGGAGTATTCCAGTCTCT | 83mer |
| C-3 | TATTCCAGTCTCTCTTGTAAGGAAATTCTACTTCAGATGGGAATAGTAGCCACCACAATTCTATGTCCATCATCATTTCCAGTCC | 83mer |
| C-4 | ATAAACATGATGTTCATGGCTTTGTGAATAAGCTTCATAAGAAGATTTCATAACCTCGGTTCCTGAAGACCTTTCTCGGACTGAAAAT | 83mer |
| C-5 | GAGGATGCCAGCCATGGACCAGATCCAGCCATCCATCCAGTGTGTGGCAATGTAATACATAGCTATGATAAACATGATGT | 83mer |
| C-6 | GTCGACAAAGTGGCGGTCTTAAGACCTCCGTTCATGATGATACGTCCAGAACCTGTCGAAGCAGAGGATGCCAGC | 83mer |

FIG. 6B

| | | |
|---|---|---|
| D-1 | GTCGACCACAGATGATTCTAACGTTATCAAGATTCTGTCAAGAAGCCTAAGTTCTTCAAGTATCAAGTGGGAGCATTGCC | 82mer |
| D-2 | GGAGCATTTGCCTATATGTACTTTCTTTCCACCAAAAATCAGCCTGGTTCTACCAAGTTTCATCTCATCCCTTCACAGTCCTAT | 82mer |
| D-3 | TTCACAGTCCTATCAGAAAGGCACAGAGATCCTAACACCCAGATCAACTAACTATGTACGTCAAAGCTAACAAGGGCATTA | 82mer |
| D-4 | CCTCTAAGAAAATCTTGCAATCAACGGTATGGTTTGGAGCGCTTAGAACTTTGCTAAGAACTACTCTCGTAATGCCCTTGTT | 82mer |
| D-5 | GGCCCGCAGCTACTCCTACTAGATTTGTCTTAAGTTTGGCAATGTGAGGGACAGTTACCGCCATATGGTCCCTAAGAAAAT | 82mer |
| D-6 | CTGCAGTTGATCAGTGCTAGGCAATCTAAGGCATTCTACGAAATGGGGTAGAATGGCTGCCACGCCGAGCCCGCAGCTACT | 82mer |
| | | |
| E-1 | CTGCAGCACAAGTTCTACTGGATCGTCAACGACCTTAGTCACCTTAAGTGGTTCGAAAAACGAGCTACAATGGCTTAA | 77mer |
| E-2 | ACAATGGCTTAAGGAGAAATCTTGTGAAGTCTCTGTCATCTACACTGGGTCATCAGTGGAGGATACAAACTCAGATG | 77mer |
| E-3 | CAAACTCAGATGAGTCCACTAAGGGTTTCGATGACAAGAAGAATCGAAATCACCGTAGAAATGCTTAACACAAGAGG | 77mer |
| E-4 | GTGATGTTGTTGTTCTCGAGTTCTGACAATTGATCTCCACTAGAGTCTTTGAGGTCTTGGCCTCTTGTTAAG | 77mer |
| E-5 | CGATACCTTGTACAACTGCATTCCTAAAGTCGTCATTGAAGTCGCTCGTCCGCATGAGTAGAAAGTGATGTTGTTG | 77mer |
| E-6 | AAGCTTGAGCTCTTACCAAGTAAAACTCTCCTCCTCCTAGTTCGACATCTATCTTCAGACTAGAATCGATACCTTGTA | 77mer |

FIG. 7

| FIG. 7A | FIG. 7B | FIG. 7C |
|---|---|---|

```
721  TAACATCAAGTTGCCACATCCTTAGATAGACCTAGAATGGAGAAGATCAATGGCATTCGTCGTCACGCCGTCGTGACTTGATGGCAATCGCTCTTTTCCCGTGGTGGTACCTTTTCGGTAT  840
721  ATTGTAGTTCAACGGTGTAGGAATGTATCTGGATCATCTCTTCTTGAGTTCCTAGTTGAAGCAGCACTACCGGTGCGGCAACACTGAACTACCCGTTAGCGAACAAGGGCCACCACATGGAAAAGCCATA  840
                                                                                                                  ─────────────→
                                                                                                                        B-6
                                                                                                                                                C-1
                                                                                                                                         ────────→

841  CCGGAACAACCCCTTCATCCGAATCACCGGATTGAGCTTTAGTTACTTTCAACTTTTACCACACAAATGGTCAGACATACGTCTGCTTCATGTTAGCCCTGTCGTCCATTCAATCGTTATGACCGC  960
841  GGCCTTGTTGGGGAAGTAGGGTTAGTGGCCTAACTCGAAATCATGAAAAGTTGAAAATGGTGTTTACCAGTCGTATGCAGACGAAGTACAATCGGACAGCAGGTAAGTTAGCAATACTGGCG  960
         ─────
          MroI                                C-2
                                       ────────→                                                                              C-3
                                                                                                                      ────────→

961  TTCAGGAGTTAAACGAGGAGTATTCCAGTCTCTTGTAAGGAAATTCTACTTCAGATGGGAATAGTAGCCACAATTCTTATGTCCATCATCATTTTCCAGTCCGAGAAGGTCTTCAGGAA  1080
961  AAGTCCCTCAATTTGCTCCATAAGGTCAGAGAACATTCCTTTAAGATGAAGTCTACCCTTATCATCGGTGTTAAGAATACAGTAGTAGTAAAAGTCAGGCTCTTCCAGAAGTCCTT  1080
                                                                                                                                   ←────────
                                                                                                                                        C-4

1081 CCGAGGTTATGAAATCTTCTTACTTATTCACAAAGCCATGAACATCATGTTTATCATAGCTATGTATTACCATTGCCACACATAGGATGGATGGGCTGGATCTGTTGGTCCATGGCTGGCAT  1200
1081 GGCTCCAATACTTTAGAAGAATGAATAAGTGTTTCGGTACTTGTAGTACAAATAGTATCGATCATAATGGTAACGGTGTGATCCTACCCACCTAGACCAGTACCGACCGTA  1200
                                                                                           ←────────
                                                                                              C-5
                                                                                                                                                      C-6
                                                                                                                                                ←────────

1201 CCTCTGCTTCGACAGTTCTGCCAAGACGGCTGTCCAAGACGGCTTAACATGTACGTATCATCATGAACGGAGTCTTAAGACCCGCCACTTGTCGACCACAGATGATTCTAAGCGTTATCAGAGATCTCGTCAAGAAGCCTAA  1320
1201 GGAGACGGAAGCTGTCAAGACGGTTCTGCCGAGAACATTCGGCCGTGAAACAGCTGGTGTCTACTAAGATTGCAATAGTTCTAGAGACAGTTCTTCGGATT  1320
                                                                                                               SalI
                                                   D-1
                                             ────────→                                                                         D-2
                                                                                                                          ────────→

1321 GTTCTTCAAGTATCAAGTGGGAGCATTGCCTATAATGGACTATATATGTACTTTCTTTCACCAAAATCAGCCTGGTTCACAGTTTCAATCTCATCCCTTCACAGTCCTATCCTTCACAGTTTCAATCTCATCCCTTCACAGTCCTATCCCTTCACAGTTTCAATCTCATCCCTTCACAGTCCTATCCTTCACAGTCCTATCCTTCACAGTCCTATCCTTCACAGTCCTATCCTTCACAGTCCTATCCTTCACAGTCCTATCCTTCACAGTCCTATCCTTCACAGTCCTATCCTTCACAGTCCTATCCTTCACAGTCCTATCAGAAAGGCACAGAGATCC  1440
1321 CAAGAAGTTCATAGTTCACCCTCGTAAACGGATATACATGAAAGAAGTGGTTTTAGTCGGACCAAGAGTCAAAGATGTCAGGATAGGAAGTAGAGTATAGAGTATTAGAGTATAGAGTATAGTGTTCCGTGTCTCTAGG  1440
```

FIG. 7B

```
  1                                                           gaattctctagactcccacc  19
 20 ATGGTTAGAACCAGAGTCCTTCTGCCCTCTTCTTCATCTCTTTCTTCGCTACACTTCATCTCCACTTCATGCATT   109
  1  M  V  R  T  R  V  L  F  C  L  F  I  S  F  F  A  T  L  H  L  I  S  T  S  C  I   30
110 TCTCAGGCTGCACTGTACCAGTTCGGATGCTCAAGCAAGTCAAAGTCTTGCTACTGCAAGAACATCAATTGGCTCGGAAGCGTCACTGCA  109
 31  S  Q  A  A  L  Y  Q  F  G  C  S  S  K  S  K  S  C  Y  C  K  N  I  N  W  L  G  S  V  T  A   60
200 TGGCGCTTATGAGAACTCCAAATCTAACAGACTCTGGACTCCGGTTTGATGAAACTTGCCAGCCAATGCTCAAGTATCAAGGTTTACACA  289
 61  C  A  Y  E  N  S  K  S  N  K  T  L  D  S  A  L  M  K  L  A  S  Q  C  S  I  K  Y  Y  T   90
290 CTGGAGGACATGAAGAACATCTACCTTAATGCAAGTAACTACCTTCGCGCTCCTGAGAAATCCGATAAGAAGACAGTTGTTTCACAACCG  379
 91  L  E  D  M  K  N  I  Y  L  N  A  S  N  Y  L  R  A  P  E  K  S  D  K  K  T  V  V  S  Q  P  120
380 TTGATGGCAAATGAGACGGCCTATCACTACTATGAGGAAAACTATGGGATCCACTTGAATTTGATGCGATCTCAATGGTGCGCATGG    469
121  L  M  A  N  E  T  A  Y  H  Y  Y  Y  E  E  N  Y  G  I  H  L  N  L  M  R  S  Q  M  C  A  W  150
470 GGCCTCGTCTTCTTCTGGGTTGCAGTTCCTCGGTGGCGCAGTCCTCGGTATTCGGCAAGAACATTATGGCAAAT                  559
151  G  L  V  F  F  W  V  A  V  L  T  A  A  T  I  L  N  I  L  K  R  V  F  G  K  N  I  M  A  N  180
560 TCTGTTAAGAAGTCTCTTATCTACCCAAGCGTTTACAAAGACTACAACGAGAGAACTTTCTATCTTTGAAACGTTTGCCATTCAACTTT   649
181  S  V  K  K  S  L  I  Y  P  S  V  Y  K  Q  Y  N  E  R  T  F  Y  L  N  K  R  L  P  F  N  F  210
```

FIG. 9A

```
 650 ACAACTCGAGGCAAAGGACTCGTAGTTCTTATCTTTGTCATTCTGACTATTCTCCACTCTCTTTCGGACATAACATCAAGTTGCCACAT  739
 211  T  T  R  G  K  G  L  V  V  L  I  F  V  I  L  T  I  L  S  F  G  H  N  I  K  L  P  H       210

740 CCTTACGATAGACCTAGATGGAGAAGATCAATGGCATTGTCTCACGCCGTGCTGACTTGATGGCAATGCTCTTTTCCCGTGTGTAC   829
 241  P  Y  D  R  P  R  W  R  R  S  M  A  F  V  S  R  R  A  D  L  M  A  I  A  L  F  P  V  V  Y  270

830 CTTTTCGGTATCCGGAACAACCCCTTCATCCCAATCACCGGATTGAGCTTTAGTACTTTCAACTTTTACCAAATGTCAGCATACGTC   919
 271  L  F  G  I  R  N  N  P  F  I  P  I  T  G  L  S  F  S  T  F  N  F  Y  H  K  W  S  A  Y  V  300

920 TGCTTCATGTTAGCCGTCGTCCATTCAATCGTTATGACCGCTTCAGGAGTATTCCAGTCTCTTGTAAGGAAATTCTAC          1009
 301  C  F  M  L  A  V  V  H  S  I  V  M  T  A  S  G  V  K  R  G  V  F  G  S  L  V  R  K  F  Y  330

1010 TTCAGATGGGGAATAGTAGCCACAATTCTTATGTCCATCATCATTTTCCAGTCCGAGAAGGTCTTCAGGAACCGAGGTTATGAAATCTTC 1099
 331  F  R  W  G  I  V  A  T  I  L  M  S  I  I  F  Q  S  E  K  V  F  R  N  R  G  Y  E  I  F    360

1100 TTACTTATTCACAAAGCCATGAACATCATGTTTATCATAGCTATGTATCATTGCCACACACTAGGATGGATGGGCTGAAGACGGAGTC 1189
 361  L  L  I  H  K  A  M  N  I  M  F  I  I  A  M  Y  H  C  H  T  L  G  W  M  G  W  I  M  S    390

1190 ATGGCTGGCATCCTCTGCTTCGACAGGTTCTGCCGAATTGTACGTATCATCATGAACGGAGTCTTAAGACCGCCACTTGTCGACCACA 1279
 391  M  A  G  I  L  C  F  D  R  F  C  R  I  V  R  I  I  M  N  G  G  L  K  T  A  T  L  S  T  T  420

1280 GATGATTCTAACGTTATCAAGATCTCTGTCAAGAAGCCTAAGTTCTTCAAGTATCAAGTGGGAGCATTTGCCTATATGTACTTTCTTTCA 1369
 421  D  D  S  N  V  I  K  I  S  V  K  K  P  K  F  F  K  Y  Q  V  G  A  F  A  Y  M  Y  F  L  S  450

1370 CCAAAATCAGCCTGGTTCTACAGTTTTCAATCTCATCCCTTCACAGTCCTATCAGAAGCACAGAGATCCTAACAACCCAGATCAACTA 1459
 451  P  K  S  A  W  F  Y  S  F  Q  S  H  P  F  T  V  L  S  E  R  N  R  D  P  N  N  P  D  Q  L  480
```

FIG. 9B

```
1460 ACTATGTAGTCAAAGTCAACAAGGGCATTACGAGAGTACTTCTTAGCAAAGTTCTAAGCGCTCCAAACCATACCGTTGATTGCAAGATT 1549
481   T  M  Y  K  S  N  K  G  I  T  R  V  L  L  S  K  Y  L  S  A  P  N  H  T  V  D  C  K  I   510
1550 TTCTTAGAGGGACCATATGGCGTAACTGTCCCTCACATTGCCAAACTTAAGAGAAATCTAGTAGGAGTAGCTCGGGGCCTCGGCGTGCA 1639
571   F  L  E  G  P  Y  G  V  T  V  P  H  I  A  K  L  K  R  N  L  V  G  V  A  A  G  L  G  V  A   570
1640 GCCATCTACCCCCATTCGTAGAATGCCTTAGATTGTCGAAAACGAGCTACACTGCCAGCGATCGTTCTACTGGATCGTCAACGACCTAGT 1729
541   A  I  Y  P  H  F  V  E  C  L  R  L  P  S  T  D  Q  L  Q  H  K  F  Y  W  I  V  N  D  L  S   570
1730 CACCTTAAGTGGTTCGAAAACGAGCTACAAATGGCTTAAGGAGAAATCTTGTGAAGTCTCTGTCATCTACACTGGTCATCAGTGGAGGAT 1819
571   H  L  K  W  F  E  N  E  L  Q  W  L  K  E  K  S  C  E  V  S  V  I  Y  T  G  S  S  V  E  D   600
1820 ACAAACTCAGATGAGTCCACTAAGGGTTTCGATGACAAGGAAGAATCTGAAATCACCGTAGAATGCCTTAACAGAGGCCAGACCTCAAA 1909
601   T  N  S  D  E  S  T  K  G  F  D  D  K  E  E  S  E  I  T  V  E  C  L  N  K  R  P  D  L  K   630
1910 GAGCTAGTGAGATCAGAGATCAAATTGTCGAGAACTCGAGAACAACTCACTTTCTACTCATGCGGACCAGCGACTTTCAATGACGAC 1999
631   E  L  V  R  S  E  I  K  L  S  E  L  E  N  N  I  T  F  Y  S  C  G  P  A  T  F  N  D  D   660
2000 TTTAGGAATGCAGTTGTACAAGGTATCGATTCTAGTCTGAAGATATCGAACTAGAGAGGAGAGTTTTACTTGGTAA 2089
661   F  R  N  A  V  V  Q  G  I  D  S  S  L  K  I  D  V  E  L  E  E  E  S  F  T  W  *          687
2090 ctt
```

FIG. 9C

FRE1 refre1

T₂ Plants

SEQUENCE LISTING

```
<160> NUMBER OF SEQ ID NOS: 38

<210> SEQ ID NO 1
<211> LENGTH: 2092
<212> TYPE: DNA
<213> ORGANISM: Artificial Sequence
<220> FEATURE:
<223> OTHER INFORMATION: Description of Artificial Sequence: Synthetic
      saccharomyces cerevisiae
<221> NAME/KEY: CDS
<222> LOCATION: (20)..(2077)

<400> SEQUENCE: 1
gaattctcta gactccacc atg gtt aga acc aga gtc ctt ttc tgc ctc ttc      52
                     Met Val Arg Thr Arg Val Leu Phe Cys Leu Phe
                      1               5                  10 atc tct ttc ttc gct aca gtc caa tcg agc gct aca ctc atc tcc act     100
Ile Ser Phe Phe Ala Thr Val Gln Ser Ser Ala Thr Leu Ile Ser Thr
             15                  20                  25 tca tgc att tct cag gct gca ctg tac cag ttc gga tgc tca agc aag     148
Ser Cys Ile Ser Gln Ala Ala Leu Tyr Gln Phe Gly Cys Ser Ser Lys
         30                  35                  40
```

-continued

| | | | | | | | | | | | | | | | | |
|---|---|---|---|---|---|---|---|---|---|---|---|---|---|---|---|---|
| tca | aag | tct | tgc | tac | tgc | aag | aac | atc | aat | tgg | ctc | gga | agc | gtc | act | 196 |
| Ser | Lys | Ser | Cys | Tyr | Cys | Lys | Asn | Ile | Asn | Trp | Leu | Gly | Ser | Val | Thr | |
| 45 | | | | | 50 | | | | | 55 | | | | | | |
| gca | tgc | gct | tat | gag | aac | tcc | aaa | tct | aac | aag | act | ctg | gac | tcc | gct | 244 |
| Ala | Cys | Ala | Tyr | Glu | Asn | Ser | Lys | Ser | Asn | Lys | Thr | Leu | Asp | Ser | Ala | |
| 60 | | | | | 65 | | | | | 70 | | | | | 75 | |
| ttg | atg | aaa | ctt | gcc | agc | caa | tgc | tca | agt | atc | aag | gtt | tac | aca | ctg | 292 |
| Leu | Met | Lys | Leu | Ala | Ser | Gln | Cys | Ser | Ser | Ile | Lys | Val | Tyr | Thr | Leu | |
| | | | | 80 | | | | | 85 | | | | | 90 | | |
| gag | gac | atg | aag | aac | atc | tac | ctt | aat | gca | agt | aac | tac | ctt | cgc | gct | 340 |
| Glu | Asp | Met | Lys | Asn | Ile | Tyr | Leu | Asn | Ala | Ser | Asn | Tyr | Leu | Arg | Ala | |
| | | | 95 | | | | | 100 | | | | | 105 | | | |
| cct | gag | aaa | tcc | gat | aag | aag | aca | gtt | gtt | tca | caa | ccg | ttg | atg | gca | 388 |
| Pro | Glu | Lys | Ser | Asp | Lys | Lys | Thr | Val | Val | Ser | Gln | Pro | Leu | Met | Ala | |
| | | 110 | | | | | 115 | | | | | 120 | | | | |
| aat | gag | acg | gcc | tat | cac | tac | tac | tat | gag | gaa | aac | tat | ggg | atc | cac | 436 |
| Asn | Glu | Thr | Ala | Tyr | His | Tyr | Tyr | Tyr | Glu | Glu | Asn | Tyr | Gly | Ile | His | |
| | 125 | | | | | 130 | | | | | 135 | | | | | |
| ttg | aat | ttg | atg | cga | tct | caa | tgg | tgc | gca | tgg | ggc | ctc | gtc | ttc | ttc | 484 |
| Leu | Asn | Leu | Met | Arg | Ser | Gln | Trp | Cys | Ala | Trp | Gly | Leu | Val | Phe | Phe | |
| 140 | | | | | 145 | | | | | 150 | | | | | 155 | |
| tgg | gtc | gca | gtc | ctt | acc | gcc | gca | act | atc | ttg | aac | att | ctc | aaa | cgc | 532 |
| Trp | Val | Ala | Val | Leu | Thr | Ala | Ala | Thr | Ile | Leu | Asn | Ile | Leu | Lys | Arg | |
| | | | | 160 | | | | | 165 | | | | | 170 | | |
| gta | ttc | ggc | aag | aac | att | atg | gca | aat | tct | gtt | aag | aag | tct | ctt | atc | 580 |
| Val | Phe | Gly | Lys | Asn | Ile | Met | Ala | Asn | Ser | Val | Lys | Lys | Ser | Leu | Ile | |
| | | | 175 | | | | | 180 | | | | | 185 | | | |
| tac | cca | agc | gtt | tac | aaa | gac | tac | aac | gag | aga | act | ttc | tat | ctt | tgg | 628 |
| Tyr | Pro | Ser | Val | Tyr | Lys | Asp | Tyr | Asn | Glu | Arg | Thr | Phe | Tyr | Leu | Trp | |
| | | 190 | | | | | 195 | | | | | 200 | | | | |
| aaa | cgt | ttg | cca | ttc | aac | ttt | aca | act | cga | ggc | aaa | gga | ctc | gta | gtt | 676 |
| Lys | Arg | Leu | Pro | Phe | Asn | Phe | Thr | Thr | Arg | Gly | Lys | Gly | Leu | Val | Val | |
| | 205 | | | | | 210 | | | | | 215 | | | | | |
| ctt | atc | ttt | gtc | att | ctg | act | att | ctc | tca | ctc | tct | ttc | gga | cat | aac | 724 |
| Leu | Ile | Phe | Val | Ile | Leu | Thr | Ile | Leu | Ser | Leu | Ser | Phe | Gly | His | Asn | |
| 220 | | | | | 225 | | | | | 230 | | | | | 235 | |
| atc | aag | ttg | cca | cat | cct | tac | gat | aga | cct | aga | tgg | aga | aga | tca | atg | 772 |
| Ile | Lys | Leu | Pro | His | Pro | Tyr | Asp | Arg | Pro | Arg | Trp | Arg | Arg | Ser | Met | |
| | | | | 240 | | | | | 245 | | | | | 250 | | |
| gca | ttc | gtc | tca | cgc | cgt | gct | gac | ttg | atg | gca | atc | gct | ctt | ttc | ccc | 820 |
| Ala | Phe | Val | Ser | Arg | Arg | Ala | Asp | Leu | Met | Ala | Ile | Ala | Leu | Phe | Pro | |
| | | | 255 | | | | | 260 | | | | | 265 | | | |
| gtg | gtg | tac | ctt | ttc | ggt | atc | cgg | aac | aac | ccc | ttc | atc | cca | atc | acc | 868 |
| Val | Val | Tyr | Leu | Phe | Gly | Ile | Arg | Asn | Asn | Pro | Phe | Ile | Pro | Ile | Thr | |
| | | 270 | | | | | 275 | | | | | 280 | | | | |
| gga | ttg | agc | ttt | agt | act | ttc | aac | ttt | tac | cac | aaa | tgg | tca | gca | tac | 916 |
| Gly | Leu | Ser | Phe | Ser | Thr | Phe | Asn | Phe | Tyr | His | Lys | Trp | Ser | Ala | Tyr | |
| | 285 | | | | | 290 | | | | | 295 | | | | | |
| gtc | tgc | ttc | atg | tta | gcc | gtc | gtc | cat | tca | atc | gtt | atg | acc | gct | tca | 964 |
| Val | Cys | Phe | Met | Leu | Ala | Val | Val | His | Ser | Ile | Val | Met | Thr | Ala | Ser | |
| 300 | | | | | 305 | | | | | 310 | | | | | 315 | |
| gga | gtt | aaa | cga | gga | gta | ttc | cag | tct | ctt | gta | agg | aaa | ttc | tac | ttc | 1012 |
| Gly | Val | Lys | Arg | Gly | Val | Phe | Gln | Ser | Leu | Val | Arg | Lys | Phe | Tyr | Phe | |
| | | | 320 | | | | | 325 | | | | | 330 | | | |
| aga | tgg | gga | ata | gta | gcc | aca | att | ctt | atg | tcc | atc | atc | att | ttc | cag | 1060 |
| Arg | Trp | Gly | Ile | Val | Ala | Thr | Ile | Leu | Met | Ser | Ile | Ile | Ile | Phe | Gln | |
| | | | 335 | | | | | 340 | | | | | 345 | | | |
| tcc | gag | aag | gtc | ttc | agg | aac | cga | ggt | tat | gaa | atc | ttc | tta | ctt | att | 1108 |
| Ser | Glu | Lys | Val | Phe | Arg | Asn | Arg | Gly | Tyr | Glu | Ile | Phe | Leu | Leu | Ile | |
| | 350 | | | | | 355 | | | | | 360 | | | | | |

-continued

| | | |
|---|---|---|
| cac aaa gcc atg aac atc atg ttt atc ata gct atg tat tac cat tgc<br>His Lys Ala Met Asn Ile Met Phe Ile Ile Ala Met Tyr Tyr His Cys<br>365                           370                         375 | 1156 |
| cac aca cta gga tgg atg ggc tgg atc tgg tcc atg gct ggc atc ctc<br>His Thr Leu Gly Trp Met Gly Trp Ile Trp Ser Met Ala Gly Ile Leu<br>380                           385                       390                   395 | 1204 |
| tgc ttc gac agg ttc tgc cga att gta cgt atc atc atg aac gga ggt<br>Cys Phe Asp Arg Phe Cys Arg Ile Val Arg Ile Ile Met Asn Gly Gly<br>                        400                       405                       410 | 1252 |
| ctt aag acc gcc act ttg tcg acc aca gat gat tct aac gtt atc aag<br>Leu Lys Thr Ala Thr Leu Ser Thr Thr Asp Asp Ser Asn Val Ile Lys<br>           415                       420                       425 | 1300 |
| atc tct gtc aag aag cct aag ttc ttc aag tat caa gtg gga gca ttt<br>Ile Ser Val Lys Lys Pro Lys Phe Phe Lys Tyr Gln Val Gly Ala Phe<br>                 430                       435                       440 | 1348 |
| gcc tat atg tac ttt ctt tca cca aaa tca gcc tgg ttc tac agt ttt<br>Ala Tyr Met Tyr Phe Leu Ser Pro Lys Ser Ala Trp Phe Tyr Ser Phe<br>445                           450                       455 | 1396 |
| caa tct cat ccc ttc aca gtc cta tca gaa agg cac aga gat cct aac<br>Gln Ser His Pro Phe Thr Val Leu Ser Glu Arg His Arg Asp Pro Asn<br>460                           465                       470                   475 | 1444 |
| aac cca gat caa cta act atg tac gtc aaa gct aac aag ggc att acg<br>Asn Pro Asp Gln Leu Thr Met Tyr Val Lys Ala Asn Lys Gly Ile Thr<br>                 480                       485                       490 | 1492 |
| aga gta ctt ctt agc aaa gtt cta agc gct cca aac cat acc gtt gat<br>Arg Val Leu Leu Ser Lys Val Leu Ser Ala Pro Asn His Thr Val Asp<br>           495                       500                       505 | 1540 |
| tgc aag att ttc tta gag gga cca tat ggc gta act gtc cct cac att<br>Cys Lys Ile Phe Leu Glu Gly Pro Tyr Gly Val Thr Val Pro His Ile<br>                 510                       515                       520 | 1588 |
| gcc aaa ctt aag aga aat cta gta gga gta gct gcg ggc ctc ggc gtg<br>Ala Lys Leu Lys Arg Asn Leu Val Gly Val Ala Ala Gly Leu Gly Val<br>525                           530                       535 | 1636 |
| gca gcc atc tac ccc cat ttc gta gaa tgc ctt aga ttg cct agc act<br>Ala Ala Ile Tyr Pro His Phe Val Glu Cys Leu Arg Leu Pro Ser Thr<br>540                           545                       550                   555 | 1684 |
| gat caa ctg cag cac aag ttc tac tgg atc gtc aac gac ctt agt cac<br>Asp Gln Leu Gln His Lys Phe Tyr Trp Ile Val Asn Asp Leu Ser His<br>                 560                       565                       570 | 1732 |
| ctt aag tgg ttc gaa aac gag cta caa tgg ctt aag gag aaa tct tgt<br>Leu Lys Trp Phe Glu Asn Glu Leu Gln Trp Leu Lys Glu Lys Ser Cys<br>           575                       580                       585 | 1780 |
| gaa gtc tct gtc atc tac act ggg tca tca gtg gag gat aca aac tca<br>Glu Val Ser Val Ile Tyr Thr Gly Ser Ser Val Glu Asp Thr Asn Ser<br>                 590                       595                       600 | 1828 |
| gat gag tcc act aag ggt ttc gat gac aag gaa gaa tct gaa atc acc<br>Asp Glu Ser Thr Lys Gly Phe Asp Asp Lys Glu Glu Ser Glu Ile Thr<br>605                           610                       615 | 1876 |
| gta gaa tgc ctt aac aag agg cca gac ctc aaa gag cta gtg aga tca<br>Val Glu Cys Leu Asn Lys Arg Pro Asp Leu Lys Glu Leu Val Arg Ser<br>620                           625                       630                   635 | 1924 |
| gag atc aaa ttg tca gaa ctc gag aac aac aac atc act ttc tac tca<br>Glu Ile Lys Leu Ser Glu Leu Glu Asn Asn Asn Ile Thr Phe Tyr Ser<br>                 640                       645                       650 | 1972 |
| tgc gga cca gcg act ttc aat gac gac ttt agg aat gca gtt gta caa<br>Cys Gly Pro Ala Thr Phe Asn Asp Asp Phe Arg Asn Ala Val Val Gln<br>           655                       660                       665 | 2020 |
| ggt atc gat tct agt ctg aag ata gat gtc gaa cta gag gag gag agt<br>Gly Ile Asp Ser Ser Leu Lys Ile Asp Val Glu Leu Glu Glu Glu Ser | 2068 |

```
                      670              675              680
ttt act tgg taagagctca agctt                                                 2092
Phe Thr Trp
    685
```

<210> SEQ ID NO 2
<211> LENGTH: 686
<212> TYPE: PRT
<213> ORGANISM: Artificial Sequence
<220> FEATURE:
<223> OTHER INFORMATION: Description of Artificial Sequence: Synthetic
      saccharomyces cerevisiae

<400> SEQUENCE: 2

```
Met Val Arg Thr Arg Val Leu Phe Cys Leu Phe Ile Ser Phe Phe Ala
 1               5                  10                  15

Thr Val Gln Ser Ser Ala Thr Leu Ile Ser Thr Ser Cys Ile Ser Gln
            20                  25                  30

Ala Ala Leu Tyr Gln Phe Gly Cys Ser Ser Lys Ser Lys Ser Cys Tyr
        35                  40                  45

Cys Lys Asn Ile Asn Trp Leu Gly Ser Val Thr Ala Cys Ala Tyr Glu
    50                  55                  60

Asn Ser Lys Ser Asn Lys Thr Leu Asp Ser Ala Leu Met Lys Leu Ala
65                  70                  75                  80

Ser Gln Cys Ser Ser Ile Lys Val Tyr Thr Leu Glu Asp Met Lys Asn
                85                  90                  95

Ile Tyr Leu Asn Ala Ser Asn Tyr Leu Arg Ala Pro Glu Lys Ser Asp
            100                 105                 110

Lys Lys Thr Val Val Ser Gln Pro Leu Met Ala Asn Glu Thr Ala Tyr
        115                 120                 125

His Tyr Tyr Glu Glu Asn Tyr Gly Ile His Leu Asn Leu Met Arg
    130                 135                 140

Ser Gln Trp Cys Ala Trp Gly Leu Val Phe Phe Trp Val Ala Val Leu
145                 150                 155                 160

Thr Ala Ala Thr Ile Leu Asn Ile Leu Lys Arg Val Phe Gly Lys Asn
                165                 170                 175

Ile Met Ala Asn Ser Val Lys Lys Ser Leu Ile Tyr Pro Ser Val Tyr
            180                 185                 190

Lys Asp Tyr Asn Glu Arg Thr Phe Tyr Leu Trp Lys Arg Leu Pro Phe
        195                 200                 205

Asn Phe Thr Thr Arg Gly Lys Gly Leu Val Val Leu Ile Phe Val Ile
    210                 215                 220

Leu Thr Ile Leu Ser Leu Ser Phe Gly His Asn Ile Lys Leu Pro His
225                 230                 235                 240

Pro Tyr Asp Arg Pro Arg Trp Arg Ser Met Ala Phe Val Ser Arg
                245                 250                 255

Arg Ala Asp Leu Met Ala Ile Ala Leu Phe Pro Val Val Tyr Leu Phe
            260                 265                 270

Gly Ile Arg Asn Asn Pro Phe Ile Pro Ile Thr Gly Leu Ser Phe Ser
        275                 280                 285

Thr Phe Asn Phe Tyr His Lys Trp Ser Ala Tyr Val Cys Phe Met Leu
    290                 295                 300

Ala Val Val His Ser Ile Val Met Thr Ala Ser Gly Val Lys Arg Gly
305                 310                 315                 320

Val Phe Gln Ser Leu Val Arg Lys Phe Tyr Phe Arg Trp Gly Ile Val
                325                 330                 335
```

```
Ala Thr Ile Leu Met Ser Ile Ile Phe Gln Ser Glu Lys Val Phe
            340                 345                 350

Arg Asn Arg Gly Tyr Glu Ile Phe Leu Ile His Lys Ala Met Asn
            355                 360                 365

Ile Met Phe Ile Ile Ala Met Tyr Tyr His Cys His Thr Leu Gly Trp
            370                 375                 380

Met Gly Trp Ile Trp Ser Met Ala Gly Ile Leu Cys Phe Asp Arg Phe
385                 390                 395                 400

Cys Arg Ile Val Arg Ile Ile Met Asn Gly Gly Leu Lys Thr Ala Thr
                    405                 410                 415

Leu Ser Thr Thr Asp Asp Ser Asn Val Ile Lys Ile Ser Val Lys Lys
                    420                 425                 430

Pro Lys Phe Phe Lys Tyr Gln Val Gly Ala Phe Ala Tyr Met Tyr Phe
                    435                 440                 445

Leu Ser Pro Lys Ser Ala Trp Phe Tyr Ser Phe Gln Ser His Pro Phe
                    450                 455                 460

Thr Val Leu Ser Glu Arg His Arg Asp Pro Asn Asn Pro Asp Gln Leu
465                 470                 475                 480

Thr Met Tyr Val Lys Ala Asn Lys Gly Ile Thr Arg Val Leu Leu Ser
                    485                 490                 495

Lys Val Leu Ser Ala Pro Asn His Thr Val Asp Cys Lys Ile Phe Leu
                    500                 505                 510

Glu Gly Pro Tyr Gly Val Thr Val Pro His Ile Ala Lys Leu Lys Arg
                    515                 520                 525

Asn Leu Val Gly Val Ala Ala Gly Leu Gly Val Ala Ala Ile Tyr Pro
                    530                 535                 540

His Phe Val Glu Cys Leu Arg Leu Pro Ser Thr Asp Gln Leu Gln His
545                 550                 555                 560

Lys Phe Tyr Trp Ile Val Asn Asp Leu Ser His Leu Lys Trp Phe Glu
                    565                 570                 575

Asn Glu Leu Gln Trp Leu Lys Glu Lys Ser Cys Glu Val Ser Val Ile
                    580                 585                 590

Tyr Thr Gly Ser Ser Val Glu Asp Thr Asn Ser Asp Glu Ser Thr Lys
                    595                 600                 605

Gly Phe Asp Asp Lys Glu Glu Ser Glu Ile Thr Val Glu Cys Leu Asn
                    610                 615                 620

Lys Arg Pro Asp Leu Lys Glu Leu Val Arg Ser Glu Ile Lys Leu Ser
625                 630                 635                 640

Glu Leu Glu Asn Asn Asn Ile Thr Phe Tyr Ser Cys Gly Pro Ala Thr
                    645                 650                 655

Phe Asn Asp Asp Phe Arg Asn Ala Val Val Gln Gly Ile Asp Ser Ser
                    660                 665                 670

Leu Lys Ile Asp Val Glu Leu Glu Glu Ser Phe Thr Trp
                    675                 680                 685

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 3
gactcgagtc gacatcg                                                  17
```

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 4
acacttatta gcacttcatg tatt                                              24

<210> SEQ ID NO 5
<211> LENGTH: 83
<212> TYPE: DNA
<213> ORGANISM: Artificial Sequence
<220> FEATURE:
<223> OTHER INFORMATION: Description of Artificial Sequence: Primer

<400> SEQUENCE: 5
gaattctcta gactccacca tggttagaac cagagtcctt ttctgcctct tcatctcttt        60
cttcgctaca gtccaatcga gcg                                               83

<210> SEQ ID NO 6
<211> LENGTH: 83
<212> TYPE: DNA
<213> ORGANISM: Artificial Sequence
<220> FEATURE:
<223> OTHER INFORMATION: Description of Artificial Sequence: Primer

<400> SEQUENCE: 6
gtccaatcga gcgctacact catctccact tcatgcattt ctcaggctgc actgtaccag        60
ttcggatgct caagcaagtc aaa                                               83

<210> SEQ ID NO 7
<211> LENGTH: 83
<212> TYPE: DNA
<213> ORGANISM: Artificial Sequence
<220> FEATURE:
<223> OTHER INFORMATION: Description of Artificial Sequence: Primer

<400> SEQUENCE: 7
caagcaagtc aaagtcttgc tactgcaaga acatcaattg gctcggaagc gtcactgcat        60
gcgcttatga gaactccaaa tct                                               83

<210> SEQ ID NO 8
<211> LENGTH: 83
<212> TYPE: DNA
<213> ORGANISM: Artificial Sequence
<220> FEATURE:
<223> OTHER INFORMATION: Description of Artificial Sequence: Primer

<400> SEQUENCE: 8
tccagtgtgt aaaccttgat acttgagcat tggctggcaa gtttcatcaa agcggagtcc        60
agagtcttgt tagatttgga gtt                                               83

<210> SEQ ID NO 9
<211> LENGTH: 83
<212> TYPE: DNA
<213> ORGANISM: Artificial Sequence
<220> FEATURE:
<223> OTHER INFORMATION: Description of Artificial Sequence: Primer

<400> SEQUENCE: 9
tgtcttctta tcggatttct caggagcgcg aaggtagtta cttgcattaa ggtagatgtt        60

-continued cttcatgtcc tccagtgtgt aaa                                          83

<210> SEQ ID NO 10
<211> LENGTH: 83
<212> TYPE: DNA
<213> ORGANISM: Artificial Sequence
<220> FEATURE:
<223> OTHER INFORMATION: Description of Artificial Sequence: Primer

<400> SEQUENCE: 10
ggatcccata gttttcctca tagtagtagt gataggccgt ctcatttgcc atcaacggtt   60
gtgaaacaac tgtcttctta tcg                                          83

<210> SEQ ID NO 11
<211> LENGTH: 80
<212> TYPE: DNA
<213> ORGANISM: Artificial Sequence
<220> FEATURE:
<223> OTHER INFORMATION: Description of Artificial Sequence: Primer

<400> SEQUENCE: 11
ggatccactt gaatttgatg cgatctcaat ggtgcgcatg gggcctcgtc ttcttctggg   60
tcgcagtcct taccgccgca                                              80

<210> SEQ ID NO 12
<211> LENGTH: 80
<212> TYPE: DNA
<213> ORGANISM: Artificial Sequence
<220> FEATURE:
<223> OTHER INFORMATION: Description of Artificial Sequence: Primer

<400> SEQUENCE: 12
ccttaccgcc gcaactatct tgaacattct caaacgcgta ttcggcaaga acattatggc   60
aaattctgtt aagaagtctc                                              80

<210> SEQ ID NO 13
<211> LENGTH: 80
<212> TYPE: DNA
<213> ORGANISM: Artificial Sequence
<220> FEATURE:
<223> OTHER INFORMATION: Description of Artificial Sequence: Primer

<400> SEQUENCE: 13
gttaagaagt ctcttatcta cccaagcgtt tacaaagact acaacgagag aactttctat   60
ctttggaaac gtttgccatt                                              80

<210> SEQ ID NO 14
<211> LENGTH: 80
<212> TYPE: DNA
<213> ORGANISM: Artificial Sequence
<220> FEATURE:
<223> OTHER INFORMATION: Description of Artificial Sequence: Primer

<400> SEQUENCE: 14
agagtgagag aatagtcaga atgacaaaga taagaactac gagtcctttg cctcgagttg   60
taaagttgaa tggcaaacgt                                              80

<210> SEQ ID NO 15
<211> LENGTH: 80
<212> TYPE: DNA
<213> ORGANISM: Artificial Sequence
<220> FEATURE:

-continued

<223> OTHER INFORMATION: Description of Artificial Sequence: Primer

<400> SEQUENCE: 15
aatgccattg atcttctcca tctaggtcta tcgtaaggat gtggcaactt gatgttatgt      60
ccgaaagaga gtgagagaat      80

<210> SEQ ID NO 16
<211> LENGTH: 80
<212> TYPE: DNA
<213> ORGANISM: Artificial Sequence
<220> FEATURE:
<223> OTHER INFORMATION: Description of Artificial Sequence: Primer

<400> SEQUENCE: 16
tccggatacc gaaaaggtac accacgggga aaagagcgat tgccatcaag tcagcacggc      60
gtgagacgaa tgccattgat      80

<210> SEQ ID NO 17
<211> LENGTH: 83
<212> TYPE: DNA
<213> ORGANISM: Artificial Sequence
<220> FEATURE:
<223> OTHER INFORMATION: Description of Artificial Sequence: Primer

<400> SEQUENCE: 17
tccggaacaa ccccttcatc ccaatcaccg gattgagctt tagtactttc aactttacc      60 acaaatggtc agcatacgtc tgc      83

<210> SEQ ID NO 18
<211> LENGTH: 83
<212> TYPE: DNA
<213> ORGANISM: Artificial Sequence
<220> FEATURE:
<223> OTHER INFORMATION: Description of Artificial Sequence: Primer

<400> SEQUENCE: 18
gcatacgtct gcttcatgtt agccgtcgtc cattcaatcg ttatgaccgc ttcaggagtt      60
aaacgaggag tattccagtc tct      83

<210> SEQ ID NO 19
<211> LENGTH: 83
<212> TYPE: DNA
<213> ORGANISM: Artificial Sequence
<220> FEATURE:
<223> OTHER INFORMATION: Description of Artificial Sequence: Primer

<400> SEQUENCE: 19
tattccagtc tcttgtaagg aaattctact tcagatgggg aatagtagcc acaattctta      60
tgtccatcat cattttccag tcc      83

<210> SEQ ID NO 20
<211> LENGTH: 83
<212> TYPE: DNA
<213> ORGANISM: Artificial Sequence
<220> FEATURE:
<223> OTHER INFORMATION: Description of Artificial Sequence: Primer

<400> SEQUENCE: 20
ataaacatga tgttcatggc tttgtgaata agtaagaaga tttcataacc tcggttcctg      60
aagaccttct cggactggaa aat      83

<210> SEQ ID NO 21
<211> LENGTH: 83
<212> TYPE: DNA
<213> ORGANISM: Artificial Sequence
<220> FEATURE:
<223> OTHER INFORMATION: Description of Artificial Sequence: Primer

<400> SEQUENCE: 21
gaggatgcca gccatggacc agatccagcc catccatcct agtgtgtggc aatggtaata    60
catagctatg ataaacatga tgt                                            83

<210> SEQ ID NO 22
<211> LENGTH: 83
<212> TYPE: DNA
<213> ORGANISM: Artificial Sequence
<220> FEATURE:
<223> OTHER INFORMATION: Description of Artificial Sequence: Primer

<400> SEQUENCE: 22
gtcgacaaag tggcggtctt aagacctccg ttcatgatga tacgtacaat tcggcagaac    60
ctgtcgaagc agaggatgcc agc                                            83

<210> SEQ ID NO 23
<211> LENGTH: 82
<212> TYPE: DNA
<213> ORGANISM: Artificial Sequence
<220> FEATURE:
<223> OTHER INFORMATION: Description of Artificial Sequence: Primer

<400> SEQUENCE: 23
gtcgaccaca gatgattcta acgttatcaa gatctctgtc aagaagccta agttcttcaa    60
gtatcaagtg ggagcatttg cc                                             82

<210> SEQ ID NO 24
<211> LENGTH: 82
<212> TYPE: DNA
<213> ORGANISM: Artificial Sequence
<220> FEATURE:
<223> OTHER INFORMATION: Description of Artificial Sequence: Primer

<400> SEQUENCE: 24
ggagcatttg cctatatgta ctttctttca ccaaaatcag cctggttcta cagttttcaa    60
tctcatccct tcacagtcct at                                             82

<210> SEQ ID NO 25
<211> LENGTH: 82
<212> TYPE: DNA
<213> ORGANISM: Artificial Sequence
<220> FEATURE:
<223> OTHER INFORMATION: Description of Artificial Sequence: Primer

<400> SEQUENCE: 25
ttcacagtcc tatcagaaag gcacagagat cctaacaacc cagatcaact aactatgtac    60
gtcaaagcta caagggcat ta                                              82

<210> SEQ ID NO 26
<211> LENGTH: 82
<212> TYPE: DNA
<213> ORGANISM: Artificial Sequence
<220> FEATURE:
<223> OTHER INFORMATION: Description of Artificial Sequence: Primer

<400> SEQUENCE: 26

```
cctctaagaa aatcttgcaa tcaacggtat ggtttggagc gcttagaact ttgctaagaa      60
gtactctcgt aatgcccttg tt                                              82

<210> SEQ ID NO 27
<211> LENGTH: 82
<212> TYPE: DNA
<213> ORGANISM: Artificial Sequence
<220> FEATURE:
<223> OTHER INFORMATION: Description of Artificial Sequence: Primer

<400> SEQUENCE: 27
ggcccgcagc tactcctact agatttctct taagtttggc aatgtgaggg acagttacgc      60
catatggtcc ctctaagaaa at                                              82

<210> SEQ ID NO 28
<211> LENGTH: 82
<212> TYPE: DNA
<213> ORGANISM: Artificial Sequence
<220> FEATURE:
<223> OTHER INFORMATION: Description of Artificial Sequence: Primer

<400> SEQUENCE: 28
ctgcagttga tcagtgctag gcaatctaag gcattctacg aaatgggggt agatggctgc      60
cacgccgagg cccgcagcta ct                                              82

<210> SEQ ID NO 29
<211> LENGTH: 77
<212> TYPE: DNA
<213> ORGANISM: Artificial Sequence
<220> FEATURE:
<223> OTHER INFORMATION: Description of Artificial Sequence: Primer

<400> SEQUENCE: 29
ctgcagcaca agttctactg gatcgtcaac gaccttagtc accttaagtg gttcgaaaac      60
gagctacaat ggcttaa                                                    77

<210> SEQ ID NO 30
<211> LENGTH: 77
<212> TYPE: DNA
<213> ORGANISM: Artificial Sequence
<220> FEATURE:
<223> OTHER INFORMATION: Description of Artificial Sequence: Primer

<400> SEQUENCE: 30
acaatggctt aaggagaaat cttgtgaagt ctctgtcatc tacactgggt catcagtgga      60
ggatacaaac tcagatg                                                    77

<210> SEQ ID NO 31
<211> LENGTH: 77
<212> TYPE: DNA
<213> ORGANISM: Artificial Sequence
<220> FEATURE:
<223> OTHER INFORMATION: Description of Artificial Sequence: Primer

<400> SEQUENCE: 31
caaactcaga tgagtccact aagggtttcg atgacaagga agaatctgaa atcaccgtag      60
aatgccttaa caagagg                                                    77

<210> SEQ ID NO 32
<211> LENGTH: 77
<212> TYPE: DNA
<213> ORGANISM: Artificial Sequence
```

```
<220> FEATURE:
<223> OTHER INFORMATION: Description of Artificial Sequence: Primer

<400> SEQUENCE: 32
gtgatgttgt tgttctcgag ttctgacaat ttgatctctg atctcactag ctctttgagg      60
tctggcctct tgttaag                                                    77

<210> SEQ ID NO 33
<211> LENGTH: 77
<212> TYPE: DNA
<213> ORGANISM: Artificial Sequence
<220> FEATURE:
<223> OTHER INFORMATION: Description of Artificial Sequence: Primer

<400> SEQUENCE: 33
cgataccttg tacaactgca ttcctaaagt cgtcattgaa agtcgctggt ccgcatgagt      60
agaaagtgat gttgttg                                                    77

<210> SEQ ID NO 34
<211> LENGTH: 77
<212> TYPE: DNA
<213> ORGANISM: Artificial Sequence
<220> FEATURE:
<223> OTHER INFORMATION: Description of Artificial Sequence: Primer

<400> SEQUENCE: 34
aagcttgagc tcttaccaag taaaactctc ctcctctagt tcgacatcta tcttcagact      60
agaatcgata ccttgta                                                    77

<210> SEQ ID NO 35
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 35
gactcgagtc gacatcgatt tttttttttt ttttt                                35

<210> SEQ ID NO 36
<211> LENGTH: 2059
<212> TYPE: DNA
<213> ORGANISM: Saccharomyces cerevisiae

<400> SEQUENCE: 36
atggttagaa cccgtgtatt attctgctta tttatatctt ttttttgctac ggttcaatcg     60 agtgctacac ttattagcac ttcatgtatt tcccaagctg cgctatacca atttggatgt    120
tctagtaaat ctaaaagttg ctactgtaaa acatcaatt ggctgggttc agtgacagca     180
tgtgcctatg agaattccaa atctaacaaa acactagaca gcgccttaat gaagttagca    240
tcccaatgtt caagcatcaa agtttatact ttagaggaca tgaagaatat ttatttaaat    300
gcgtcaaatt atttgagagc acctgagaaa agtgataaaa aaaccgtggt tagtcaaccg    360
ctcatggcga acgagacagc gtatcattat tattatgagg aaaattatgg tatccatctt    420
aacctaatgc gctctcaatg gtgcgcttgg ggtctcgtct tcttctgggt gggtgtgctt    480
actgcagcca ctatcttgaa cattctgaaa agggtgtttg gtaagaacat catggcaaac    540
tccgtcaaaa aatcacttat ttatccttct gtttacaaag attataatga acgaactttt    600
tatttatgga agcgtctacc atttaatttt acaactcgag gcaagggtct cgtcgtatta    660
```

-continued

```
attttttgtta ttttgactat attatctctc agttttggtc ataatattaa acttccacac      720
ccatatgata ggcccagatg gagaagaagt atggcctttg tgagtcgtag agcagacttg      780
atggccattg cacttttccc agtagtctat ctattcggaa taagaaataa tcccttcatc      840
cctataacag ggctttcctt ttctacattt aatttctatc ataaatggtc tgcctacgtt      900
tgtttcatgt tggccgttgt acactcaatt gtcatgaccg cctcgggagt gaaaagaggt      960
gtgtttcaaa gtctggttag gaaattttac tttaggtggg gtatagtggc aacgatatta     1020
atgtctatta ttattttcca aagtgaaaaa gtatttagaa atagagggta tgagatattc     1080
cttcttattc ataaagcgat gaatattatg ttcattattg ccatgtacta ccattgtcac     1140
accctgggct ggatgggttg gatttggtca atggctggta ttttatgctt tgatagattc     1200
tgcaggattg ttagaataat catgaatggt ggcttgaaaa ctgctacttt gagtaccact     1260
gatgattcta atgttattaa atttcagta aaaaaaccaa agttttcaa gtaccaagta      1320 ggagctttcg catacatgta tttcttatca ccaaaaagtg catggttcta tagttttccaa     1380 tcacatccat ttacagtatt atcggaacga caccgtgatc caaacaatcc agatcaattg     1440
acgatgtacg taaaggcaaa taaggtatc actcgagttt tgttatcgaa agttctaagt     1500
gctccaaatc atactgttga ttgtaaaata ttccttgaag gcccatatgg tgtaacggtt     1560
ccacatatcg ctaagctaaa aagaaatctg gtaggtgtag ccgctggttt gggtgttgcg     1620
gctatttatc cgcactttgt cgaatgttta cggttaccat ctactgatca acttcagcat     1680 aaatttact ggattgttaa tgacctatcc catttgaaat ggtttgaaaa tgaattgcaa     1740
tggttaaagg agaaaagttg tgaagtctca gtcatatata ctggttccag tgttgaggac     1800
acaaattcag atgagagtac aaaaggtttt gatgataaag aagaaagcga aatcactgtt     1860
gaatgtctca ataaaagacc tgatttgaaa gaactagtgc gctcggaaat aaaactctca     1920
gaactagaga ataataatat tacctttat tcctgcgggc cagcaacgtt taacgacgat     1980
tttagaaatg cagtggtcca aggtatagac tcttccttga agattgacgt tgaactagaa     2040
gaagaaagtt ttacatggt                                                  2059
```

<210> SEQ ID NO 37
<211> LENGTH: 180
<212> TYPE: DNA
<213> ORGANISM: Saccharomyces cerevisiae
<220> FEATURE:
<221> NAME/KEY: CDS
<222> LOCATION: (1)..(180)

<400> SEQUENCE: 37

```
tcc gtc aaa aaa tca ctt att tat cct tct gtt tac aaa gat tat aat         48
Ser Val Lys Lys Ser Leu Ile Tyr Pro Ser Val Tyr Lys Asp Tyr Asn
  1               5                  10                  15 gaa cga act ttt tat tta tgg aag cgt cta cca ttt aat ttt aca act         96
Glu Arg Thr Phe Tyr Leu Trp Lys Arg Leu Pro Phe Asn Phe Thr Thr
             20                  25                  30 cga ggc aag ggt ctc gtc gta tta att ttt gtt att ttg act ata tta        144
Arg Gly Lys Gly Leu Val Val Leu Ile Phe Val Ile Leu Thr Ile Leu
         35                  40                  45 tct ctc agt ttt ggt cat aat att aaa ctt cca cac                        180
Ser Leu Ser Phe Gly His Asn Ile Lys Leu Pro His
     50                  55                  60
```

<210> SEQ ID NO 38
<211> LENGTH: 60
<212> TYPE: PRT

```
<213> ORGANISM: Saccharomyces cerevisiae

<400> SEQUENCE: 38

Ser Val Lys Lys Ser Leu Ile Tyr Pro Ser Val Tyr Lys Asp Tyr Asn
 1               5                  10                  15

Glu Arg Thr Phe Tyr Leu Trp Lys Arg Leu Pro Phe Asn Phe Thr Thr
            20                  25                  30

Arg Gly Lys Gly Leu Val Val Leu Ile Phe Val Ile Leu Thr Ile Leu
        35                  40                  45

Ser Leu Ser Phe Gly His Asn Ile Lys Leu Pro His
    50                  55                  60
```

US 6,849,724 B1

METHOD FOR TRANSFORMING PLANT, THE RESULTANT PLANT AND GENE THEREOF

TECHNICAL FIELD

This invention relates to a method for transforming a useful plant by introducing a gene of another species into the useful plant. More particularly, the present invention pertains the method for transforming the useful plant characterized in that the region of a factor relating to the poly (A) addition of the mRNA of the useful plant to be transformed contained in the base sequence of the gene of the other species is modified into another base sequence not relating to the poly (A) addition of the mRNA without substantially altering the function of the protein encoded by the gene to be introduced, the useful plant produced by it, a nucleic acid in which base sequence used thereto is modified, and a method for producing the said nucleic acid.

BACKGROUND ARTS

Growth of plants needs great numbers of nutrients. The plants absorb most of these nutrients necessary for growth from roots. The plants, which can not absorb nutrients in soil due to having hereditary low enzyme activities required for absorption of nutrients, are known.

For example, iron is an essential element for almost all organisms, and is essentially required for large numbers of enzymes involved in functioning cells such as photosynthesis and respiration. Iron solubilized in soil exists mainly in the form of Fe(III) chelate [in some case, Fe(II) chelate]. In general, Fe(II) is prevalently absorbed as compared with Fe(III) by plants, but the absorption depends on plant species.

Plants have two types of mechanisms of iron uptake, i.e. absorption mechanism (I) (refer to FIG. 1) and absorption mechanism (II) (refer to FIG. 2) (Mori, 1994).

The absorption mechanism (I) shown in FIG. 1 consists of: (1) release of proton into the rhizosphere (Olsen and Brown, 1980), (2) increased reducing activity of Fe(III) in cell membrane of roots (Brown et al., 1961 and Chaney et al., 1972), and (3) excretion of reduced and chelating substances from roots (1ether et al., 1981). Namely, Fe(III) is chelated by the released chelating substance, and Fe(II)-chelate in the free space of roots is reduced to Fe(II) on the cell membrane by ferric-chelate reductase and is absorbed through Fe(II) transporter. It is also thought that the proton is released into the rhizosphere and activity of reductase is increased by lowering pH in the free space. However, the problem is known that since reducing activity of Fe(III) is inhibited by higher pH, strong pH buffering action due to high concentration of carbonate anion results to cause lime chlorosis (Marchner et al., 1986).

Absorption mechanism (II) shown in FIG. 2 is specific to grass and consisting of: (1) synthesis of mugineic acids (phytosiderophore), (2) release of mugineic acids into the rhizosphere, (3) formation of soluble complex of iron and mugineic acids, and (4) absorption of mugineic acids-iron complex by plants body (Takagi, 1976 and Takagi et al., 1984). The iron uptake mechanism by such the absorption mechanism (II) observed in grass has advantage not to be inhibited by higher pH.

Yeast (*Saccharomyces cerevisiae*), a model organism of eukaryote, performs iron absorption similar to the above absorption mechanism (I). Since in studies on the gene level in the higher plants, Fe(II) transporter has cloned by complementation of iron absorption mutant of yeast (Eida et al., 1996), no detailed mechanism of iron absorption has been studied.

Contrary to that, the mechanism in yeast (*Saccharomyces cerevisiae*) has been studied in detail. Absorption of iron in yeast is initiated by a reduction of Fe(III) to Fe(II) by ferric-chelate reductase FRE1 and FRE2 (Dancis et al., 1990,1992, Georgatsou and Alexandraki, 1994). In the mechanism for uptake of reduced Fe(II) into cells, high affinity absorption mechanism and low affinity absorption mechanism are known.

In the absorption of iron by the high affinity absorption mechanism, after reoxidation of Fe(II) by multicopper oxidase FET3 (Askwith et al., 1994), Fe(II) may be incorporated into cells by ferric transporter FTR1 (Stearman et al., 1996). Copper is required in the reoxidation of divalent iron (Dancis et al., 1994, Klomp et al., 1997), and copper supplying pathway to FET3 has also studied (Yuan et al., 1995 and Lin et a, al., 1997).

Absorption of iron by the low affinity absorption mechanism may be performed by an action of Fe(II) transporter FET4 (Dix et al., 1994, 1997).

Such the iron absorption mechanism in yeast may be applied to plants, and plants which can be grown in the iron deficient soil may be created.

For that purpose, we have created transgenic tobacco, to which FRE1 gene of yeast provided by Dr. Dancis (NIH) was transformed (Yamaguchi, 1995).

However, in the transgenic tobacco, to which FRE1 gene was transformed, the reducing activity was not changed as compared with that of wild type. As a result of Northern hybridization analysis, the transcriptional product of yeast gene FRE1 in tobacco was so small as 0.9 kb.

Example of such incomplete transcription, in which gene of another species is transformed into the higher plant, is gene group Cry encoding δ-endotoxin (insecticidal protein) of *Bacillus thuringiensis*. More than 42 Cry genes have been known and are classified into 4 classes (cryI–cryIV) (Whiteley and Schnepf, 1986). The gene encoding this insecticidal protein was introduced into the higher plant, but neither expression nor extremely low expression was found.

This may be caused by (1) difference in codon usage, (2) high AT content in Cry gene, (3) unstable in mRNA, and (4) a partial splicing of Cry gene as intron.

A preparation of the transgenic plant with high expression of protein has been reported. Namely, in order to express Cry gene group efficiently in the higher plant, base sequence of Cry gene is modified to arrange with base sequence of the plant, and the primer is synthesized, then is completely synthesized by PCR (Perlak et al., 1991, Fujimoto et al., 1993, and Nayak et al., 1997).

Although transformation of the higher plant by introducing gene of the another organism species has known, the expression thereof was not sufficient. Various reasons have been provided as described in the above.

We have made extensive studies on factors for achieving the sufficient expression of a gene in a higher plant which has been transformed by introducing the above gene encoding a protein having a function carried by another organism so as to impart the function in the useful higher plant, and found that base sequence of the factor relating to the poly(A) addition of the mRNA of the transformed plant is an important part of the expression.

Consequently, the present invention provides a method for expressing the introduced gene in the transgenic higher plant with high efficiency, the said transgenic higher plant, and a method for modifying gene therefor.

DISCLOSURE OF THE INVENTION

The present invention relates to a method for transforming a useful plant by introducing another gene into the useful plant characterized in that the region of a factor relating to the poly(A) addition of the mRNA of the useful plant to be transformed contained in the base sequence of the said another gene is modified into another base sequence not relating to the poly(A) addition of the mRNA without substantially altering the function of the protein encoded by the gene to be introduced. Example of the region of a factor relating to the poly(A) addition of the mRNA is preferably AATAAA like base sequence, further the said region of a factor relating to the poly(A) addition of the mRNA is preferably the region existing downstream of the GT-rich base sequence. Further, modification of the base sequence of the said region is preferably carried out based on the codon usage of the transformed useful plant.

In the method of the present invention, it is preferable that base G and T rich region in the gene to be introduced is small; difference in content of base G and C within whole region of the gene to be introduced is small; the sequence has no ATTTA sequence; and/or upstream of the initiation codon of the gene to be transferred has Kozak sequence.

Further, the present invention relates to the transformed useful plant, which can be produced by the method of the present invention. The transformed useful plant of the present invention can be the organism and the seed and has no limitation in the form.

Further, the present invention relates to a nucleic acid, especially DNA, having the modified base sequence, which can be used by the above transforming method.

The base sequence of the nucleic acid of the present invention is a modified base sequence which can be expressed in the transformed useful plant with high efficiency, and, for example, is a factor relating to the poly(A) addition of mRNA of the said useful plant, and is characterized in that a part of factor relating to the said poly(A) addition is replaced by the other base sequence, further the said base sequence has small G- and T-rich region of the base in the gene to be introduced, has small difference between G- and C-content of the base throughout the gene to be introduced, has no ATTTA sequence and/or preferably the upstream of the initiation codon of the gene to be introduced has Kozak sequence.

Further, the present invention relates to a method for production of the above nucleic acids characterized in that the above nucleic acids are divided into several fragments and these fragments are ligated.

BRIEF DESCRIPTION OF DRAWINGS

FIG. 3: A position of poly(A) addition in higher plant (SEQ ID NOS: 37 & 38).

FIG. 4: G- and T-rich sequence (SEQ ID NO: 36) in yeast gene FRE1.

FIG. 5: Schematic illustration of refre1 synthesis.

FIG. 6: Sequence of 30 primers (SEQ ID NOS: 5–34, respectively, in order of appearance) used in the synthesis of refre1.

FIG. 9: Total sequence of designed refre1 (SEQ ID NOS: 1 & 2).

Left: Digestion by EcoRI and HindIII

Right: Digestion by HindIII

No.1–No.2: Transformant

W.T: wild type

Figure 15:
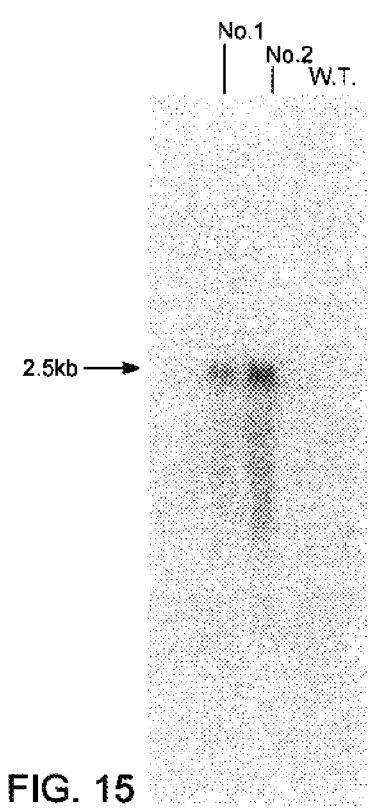

FIG. 15: Result of Northern hybridization of the transformant using refre1 as a probe.

No.1–No.2: Transformant

W.T: wild type.

Figure 16:

FIG. 16: A photograph showing activity of ferric-chelate reductase in roots indicating red coloring of BPDS-Fe(II) complex by Fe(II).

Left: Wild type showing no red coloring.

Right: Transformant showing red coloring in roots.

Figure 17:
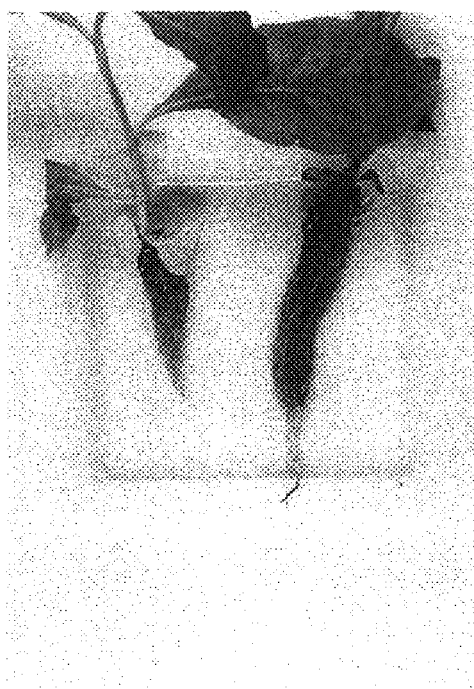

FIG. 17: Photograph showing replicate experiment of the same as in FIG. 16 using another transformant. Red coloring is observed in the transformant (right).

Figure 18:
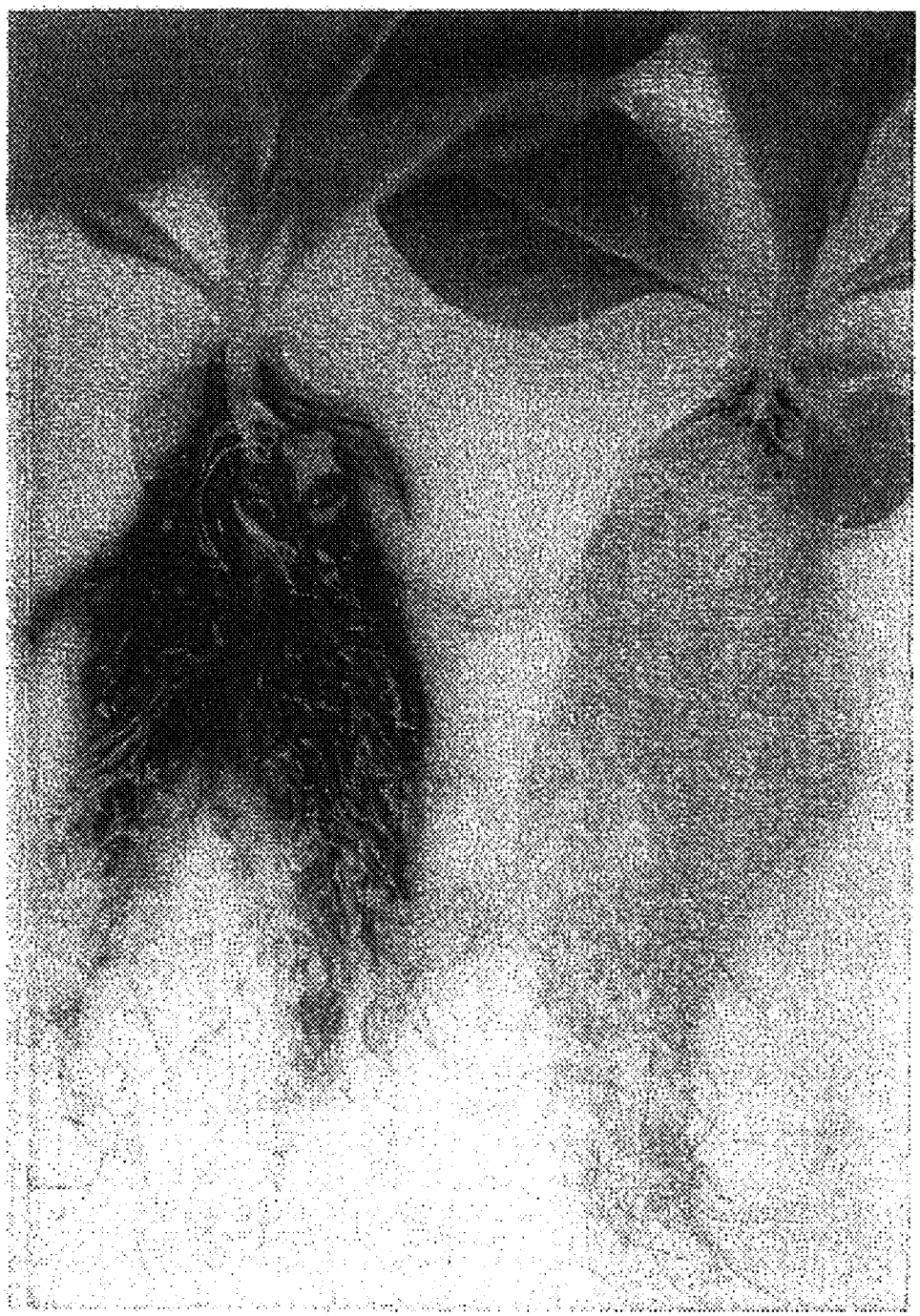

FIG. 18: Photograph showing activity of ferric-chelate reductase by red coloring of BPDS-Fe(II) complex in roots, using second generation of plant obtained from seeds of the transformant. Red coloring of BPDS-Fe(II) complex is observed in the second generation of the transformant (left).

BEST MODE FOR CARRYING OUT THE INVENTION

The useful plants transformed in the present invention are no limitation, if these are industrially used plants such as foods and pharmaceuticals, and are preferably higher plants such as grains, vegetables, fruits and tobacco.

Another gene introduced in the present invention is not limited, if it is useful for plants and has no detrimental effects for plants and human. It may be directly useful gene for plants and gene providing resistance against chemicals such as herbicide, and is preferably enzyme derived from organisms such as bacteria and yeast. For example, ferric-chelate reductase FRE1 of yeast involving absorption of iron is preferable.

We have found that in a transformed plant, factors affecting expression of introduced gene may be a base sequence which determines addition of poly(A) of mRNA. Further, we have found that in the upstream of the base sequence, which defines addition of poly(A), GT-rich base sequence is necessary. Namely, in the presence of GT-rich base sequence, addition of poly(A) is determined in plants, subsequently mRNA is split at the position after 10–30 bp from the poly(A) signal, for example AATAAA like base sequence, then poly(A) is added by an action of poly(A) polymerase. Accordingly, in case that the introduced gene has such the base sequence, in the transgenic plants, full length mRNA can not be expressed, and mRNA is split in the position after 10–30 bp from the poly(A) signal having AATAAA like base sequence.

Consequently, the present invention is characterized in that the poly(A) signal of plant in the introduced gene, for example AATAAA like base sequence, preferably GT-rich base sequence, is modified to another base sequence.

A method of design for modifying base sequence is, at first, codon is selected for not to change amino acid sequence encoded by gene to be introduced. Amino acid sequence can be changed, if the sequence has not substantial effect for function for protein, preferably the amino acid sequence may not be changed.

In case that multiple numbers of codons, which encode an amino acid, is known, the codon having high rate of usage in the plant is preferably selected by considering the codon usage of the plant to be transformed.

Further, not only modification of base sequence of poly (A) signal but also deletion of GT-rich base sequence is preferable. Especially, in case that GT-rich base sequence exists with high proportion, since possibility of splitting mRNA in the region of poly(A) signal like base sequence appearing in the downstream of the GT-rich base sequence is high, a modification for reducing amount of CT content in such the region is important.

Further, in the present invention, in addition to the above modification, it is preferable to modify in order to make smaller difference between G- and C-content of bases throughout the full region of gene to be introduced. More preferably, the sequence should not contain ATTTA sequence, which is known as unstable sequence of mRNA, and/or the sequence has Kozak sequence, which is known as a sequence for effective translation of mRNA in the eukaryote, in the upstream of the initiation codon of gene to be introduced.

The method of the present invention includes a modification of base sequence combined further with usual method of modification to the above modification of base sequence.

The method for modification of base sequence can be made without limitation by known various methods. For example, any conventional method of modification by point mutation and splitting with restriction enzyme can be applied.

Further, in case that large numbers of base have to be modified or gene itself to be introduced has short length, it can be prepared by synthesis. As explained later concretely, even if length of gene is long, the gene is divided into several fragments, and each fragment, which is amplified by PCR, is ligated using restriction enzymes, then gene having modified base sequence can be prepared.

The method of the present invention is further explained more concretely, but the method of the present invention can not be limited within the scope of the following explanation, and the broad application thereof based on the said explanation can be performed by the person skilled in the art.

We have tried to study the reason why length of mRNA of yeast FRE1, which was introduced into tobacco, was short (0.9 kb). As for the reasons for incomplete length of transcriptional product of yeast ferric-chelate reductase FRE1, which was introduced in tobacco, two possibilities were considered, i.e.

(1) a part of mRNA was spliced as intron, and (2) a transcription was terminated within coding region.

As a result of further analysis by RT-PCR, it was found that poly(A) addition occurred within coding region in the transgenic tobacco, to which FRE1 gene was transformed.

Example of the confirmed expression of yeast gene introduced into the higher plant is invertase (Hincha, 1996). In the present experiment, new knowledge, in which these is a case that full length mRNA can not be synthesized even in the same eukaryotic gene by introducing FRE1 gene, could be obtained.

Reason why full length mRNA could not be synthesized in the FRE1 transformed transgenic tobacco was addition of poly(A) within the coding region of FRE1.

A poly(A) site is not limited within one position, and in the upstream of each poly(A) site, AAUAAA like base sequence, putative poly(A) signal region was observed. However, although several AAUAAA like sequences were observed at 5'-site of FRE1, the poly(A) addition was not observed in these positions.

It may be a GU-rich sequence located in the upstream of the poly(A) signal to determine addition of poly(A) in plant. Namely, if GU-rich sequence exists, addition of poly(A) may be occured in the plant, and in the position of "PyA", which is located at the distance of 10–30 bp from the subsequently appeared AAUAAA like sequence, mRNA is splitted, then the poly(A) may be added by an action of poly(A) polymerase.

In conclusion, the fact that GU-rich sequence, which has no relation to addition of poly(A) in yeast, determines addition of poly(A) in plant, is a cause for not forming full length mRNA in the transgenic tobacco, to which FRE1 is transformed.

A sequence of ferric-chelate reductase FRE1 having GT-rich region is shown in FIG. 4. In FIG. 4, the boxed sequences are thought to be GT-rich regions.

As a result, in order to express ferric-chelate reductase FRE1 in tobacco, deletion of GT-rich sequence from FRE1 gene may be effective. However, at present, as for the sequence, which determines addition of poly(A) in plant, there may be only known that a consensus sequence may be GU-rich and the sequence is not completely determined. So long as the exact consensus sequence has not been known, there may be possibility not to be obtainable the fill length mRNA by only changing the sequence. We have, therefore, tried to design base sequence corresponding to codon usage of plants to be transformed without changing amino acid sequence of FRE1 in order to synthesize full length mRNA in plant.

In order to express yeast ferric-chelate reductase in tobacco, we have redesigned base sequence corresponding well to the codon usage of tobacco without changing amino acid sequence of FRE1. In design of base sequence, the following points are considered.

(1) GT-rich region is eliminated;

(2) Base sequence AATAAA, which may be a poly(A) signal and the similar base sequence are eliminated;

(3) In order to confirm easily the base sequence, restriction sites are set at the position in about every 400 bp (417–436 bp), and the sequence is divided in 5 segments;

(4) Base sequence, ATTTA sequence (Ohme-Takagi, 1993), which is called as unstable sequence of mRNA, is eliminated;

(5) In order not to make difference between base content G and C in whole region, position of codons are replaced; and (6) Kozak sequence, which is a sequence for effectively translating mRNA in eukaryote (Kozak, 1989) is attached prior to the initiation codon.

The thus designed modified base sequence of yeast ferric-chelate reductase FRE1 is shown in Sequence listing, SEQ ID NO: 1. Amino acid sequence thereof is shown in SEQ ID NO: 2.

The designed gene is designated as reconstructed FRE1 (hereinafter designates as "refre1").

The refre1 of the present invention is synthesized by dividing into 5 segments (A–E) as shown in FIG. 5.

A segment A consists of a sequence of 1–434 bp, in which restriction sites are designed as in base 1: EcoRI, base 7: XbaI and base 429: BamHI.

A segment B consists of a sequence of 429–845 bp, in which restriction sites are designed as in base 429: BamHI and base 840: MroI.

A segment C consists of a segment of 840–1275 bp, in which restriction sites are designed as in base 840: MroI and base 1270: SalI.

A segment D consists of a segment of 1270–1696 bp, in which restriction sites are designed as in base 1270: SalI and base 1691: PstI.

A segment E consists of a segment of 1691–2092 bp, in which restriction sites are designed as in base 1691: PstI, base 2081: SacI and base 2087: HindIII.

Each segment A–E, each consisting of sequence having 417–436 bp, is synthesized using 6 primers having 77–83 mer, respectively. Thirty primers used, from A-1 to E-6, are shown in FIG. 6. These base sequence are shown in sequence listings, SEQ ID NO: 5 SEQ ID NO: 34.

Among primers in the segments, –1, –2 and –3 are sense strands, and primers –4, –5 and –6 are anti strands. Primers are designed so as to have complementary base sequence consisting of 12 or 13 bp in the 3' end for primers –3 and –4, and overlapping sequence consisting of 12 or 13 bp in 3' end for primers –1 and –2, –2 and –3, –4 and –5, and –5 and –6. The primer –1 and –6 is designed to have restriction site at the base 1 in 5' end.

Figure 1:
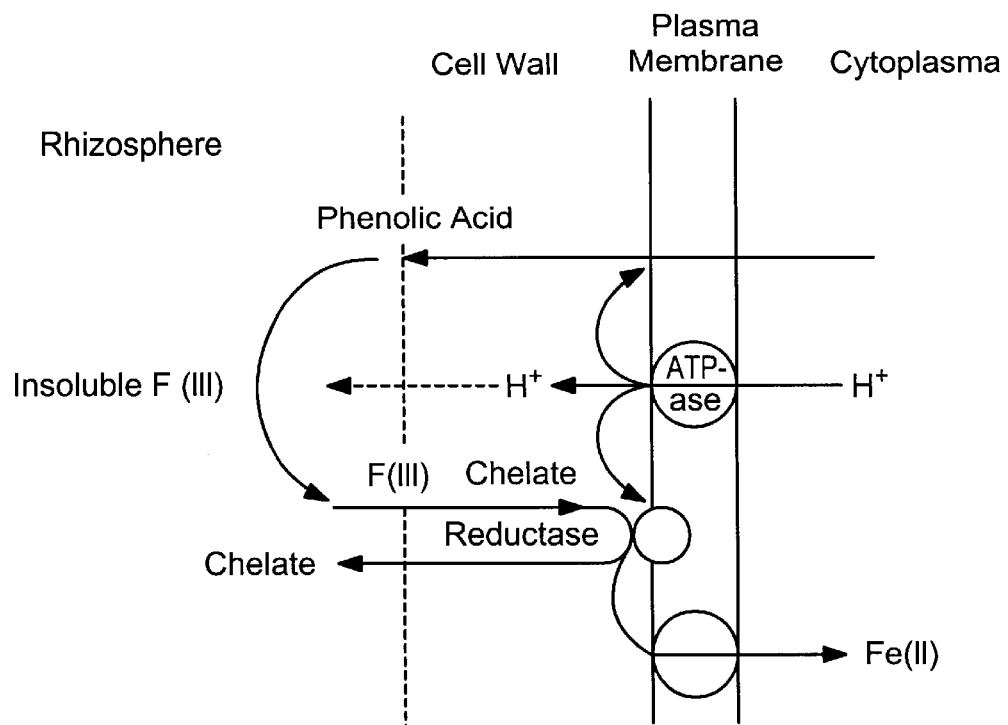
FIG. 1: Absorption mechanism (I) of iron in plants.
Figure 2:
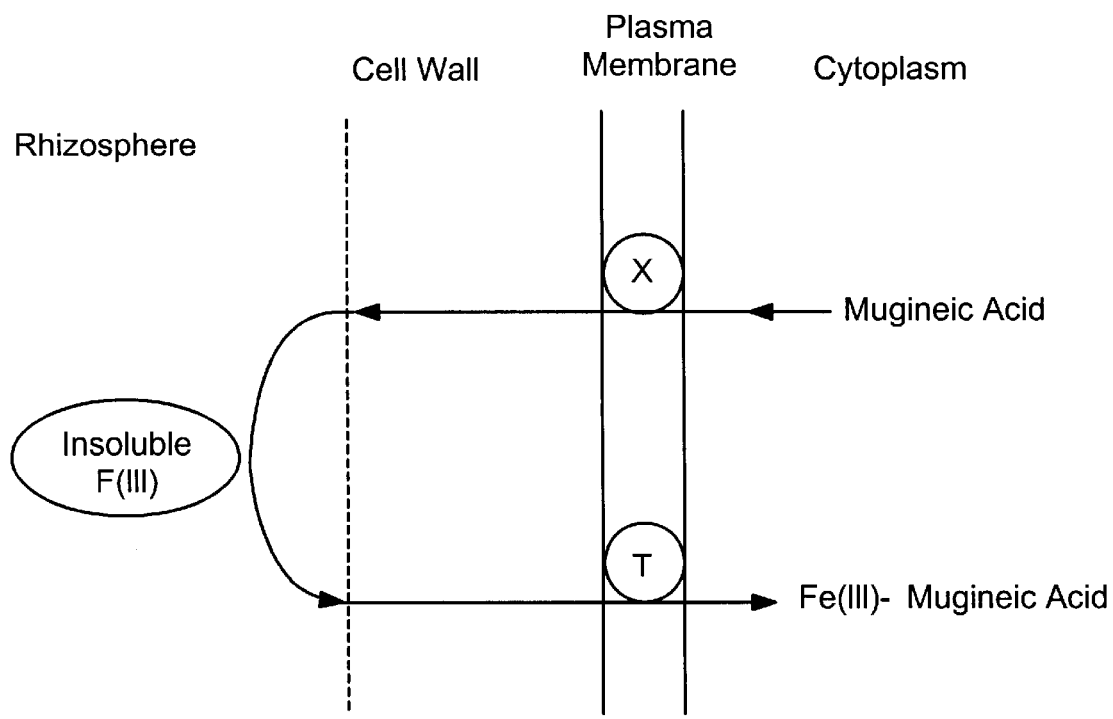
FIG. 2: Absorption mechanism (II) of iron in plants.
Figure 7A:
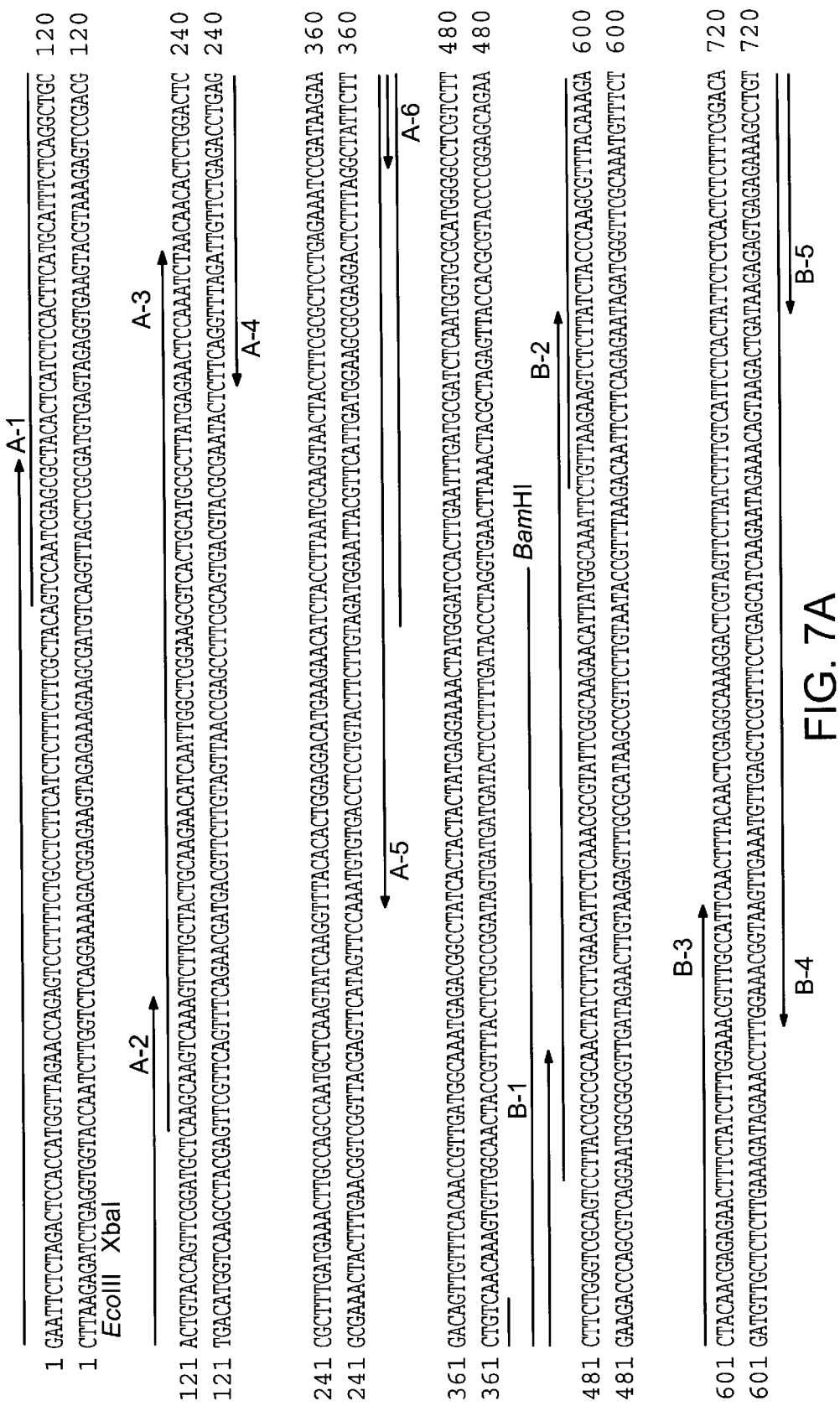
FIG. 7: Relationship between refre1 sequence (SEQ ID NO: 1) and primers (SEQ ID NOS: 5–34, respectively, in order of appearance).
Figure 7C:
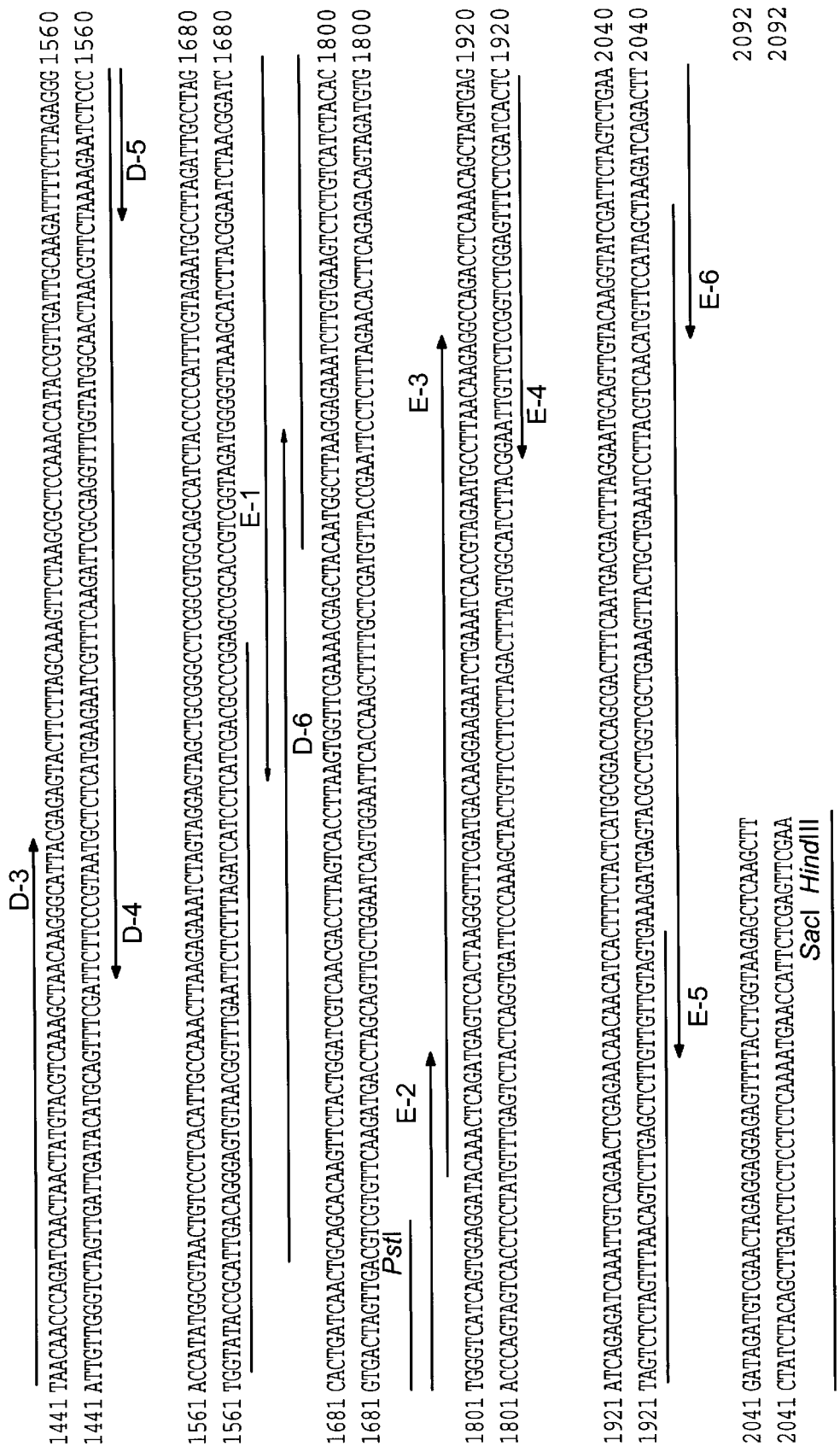

Relationship between these primers and the designed base sequences is shown in FIG. 7.

Respective segments A–E are prepared by PCR using primers synthesized according to the above base sequence (refer to FIG. 5).

After the reaction mixture of third step PCR was electrophoresed with 0.8% agarose gel, bands having expected length (417–436 bp) were cut and purified, then were cloned into plasmid pT7Blue (R) vector (supplied by Takara Corp.). The base sequences of the obtained clones were confirmed and the clones having exact base sequences were selected by applying fluorescent DNA sequencer DSQ-1000L (made by Shimadzu Corp.).

Figure 8:
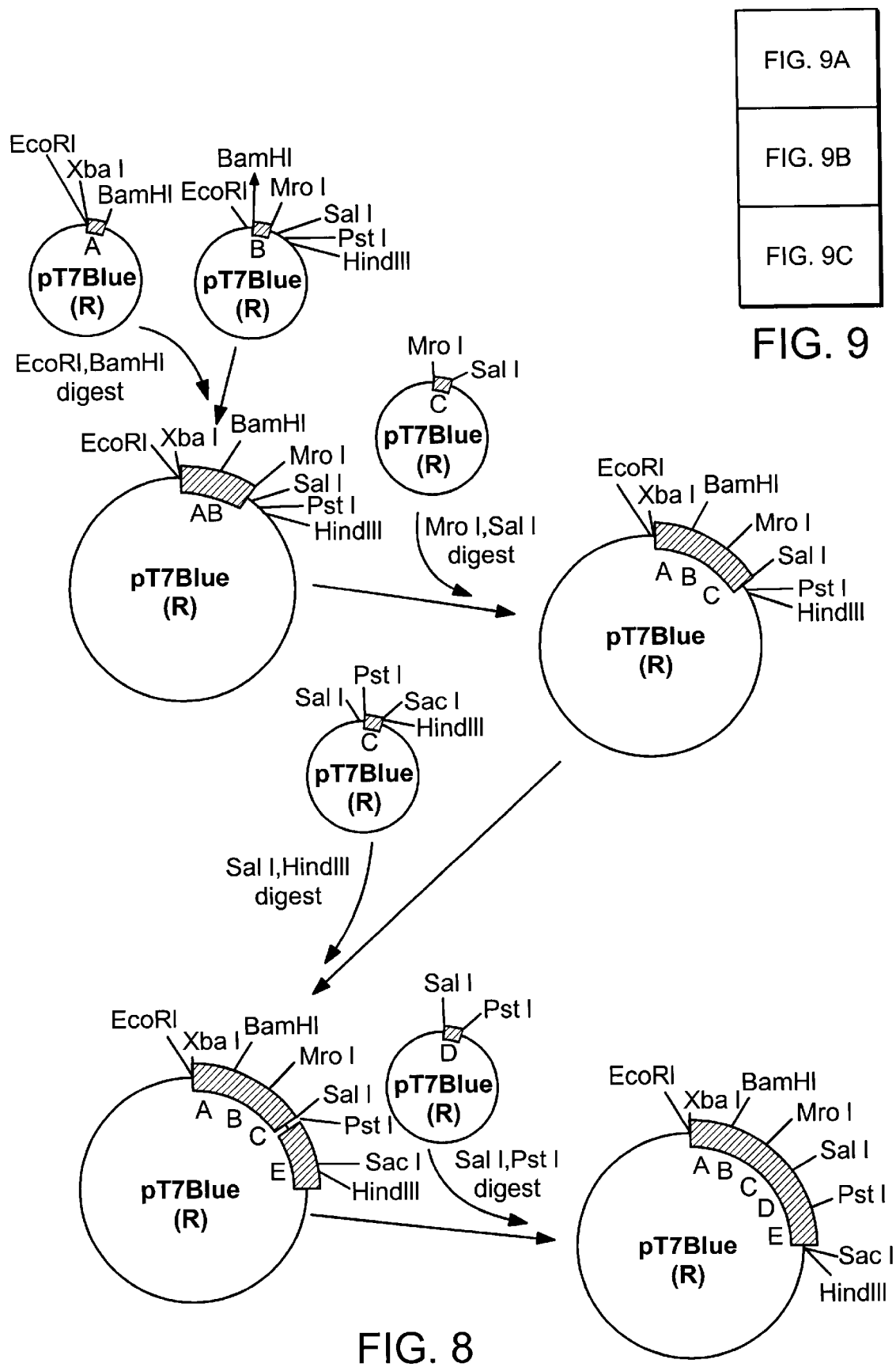
FIG. 8: Preparative scheme of full length refre1.

Segments having exact sequences were obtained and full length refre1 was prepared by applying restriction sites according to methods shown in FIG. 8.

Direction of insertion in segments B and E is essentially required for preparation of full length. In other segments, the segments containing exact base sequence were used without relation to direction of the insertion.

Total base sequence of the obtained refre1 is shown in FIG. 9. Specific features of sequence of refre1 are:

(1) 75.3% of homology to the original FRE1 (100% homology in amino acid sequence);

(2) lb have no sequence consisting of only G or T which is continuously linked more than 8 bases;

(3) It does not contain not only a sequence AATAAA but also sequences replaced by any one of bases in the above sequence;

(4) It does not contain a sequence ATTTA; and (5) No difference is observed in GC content through the whole region of the sequence.

Figure 10A:
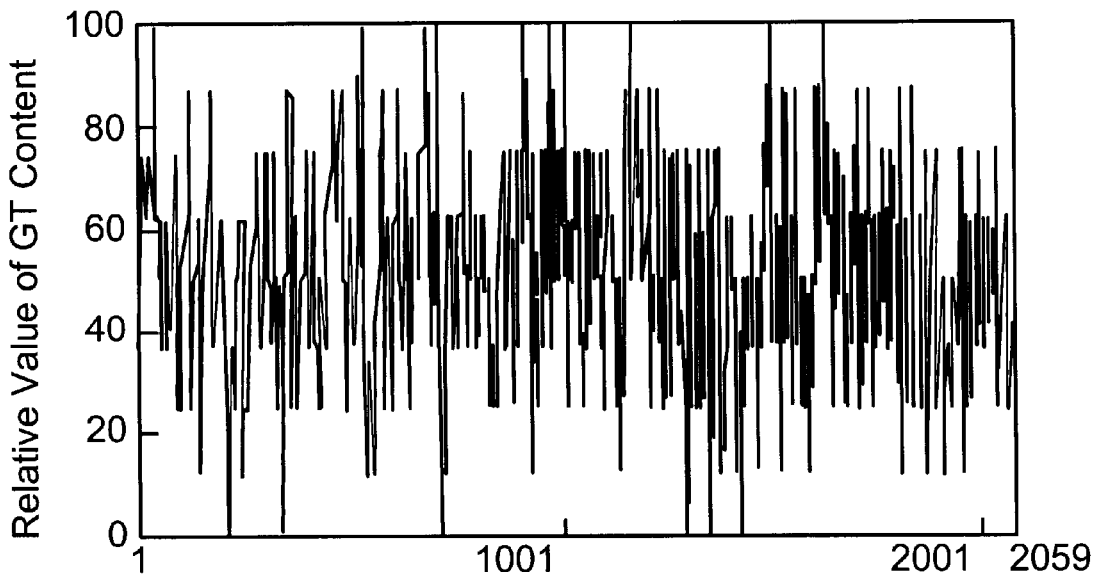
FIG. 10: Graphical illustration of G- and T-contents in FRE1 (upper level) and refre1 calculated by continued 8 base unit.
Figure 10B:
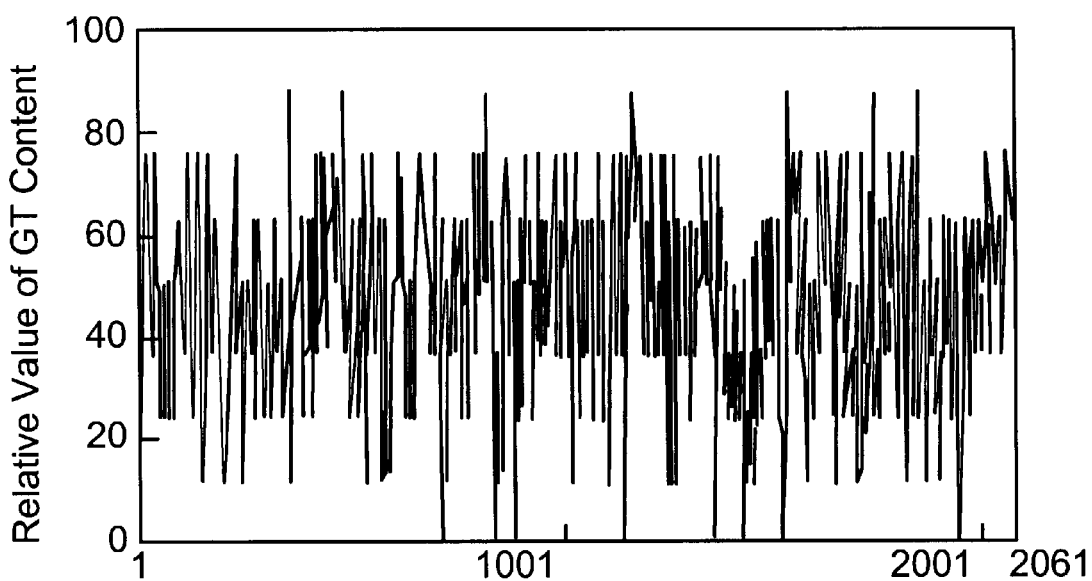

FIG. 10 shows decreased numbers of sequences consisting of serial G and T in refre1 as compared with the original FRE1. This illustrates GT content of serial 8 bases in the FRE1 and refre1 sequences. As shown in FIG. 10, uniformity of GT content in refre1 is demonstrated as compared with the original FRE1.

The thus synthesized gene refre1 is introduced into tobacco (*Nicotiana tabacum* L. var. SRI). As a result of transformation, 68 kanamycin resistant plants were reproduced. In order to confirm transformation of the objective gene in the reproduced plant and its copying number, genomic Southern hybridization was conducted. As a result, one to several copied plants of the transformant, refre1 gene was confirmed.

A method from gene introduce into plant cells to reproduction of plant can be performed by conventional method, for example, as described in "Laboratory Manual on functional analysis of plant gene" (Maruzen) [ref. (4)].

Figure 11:
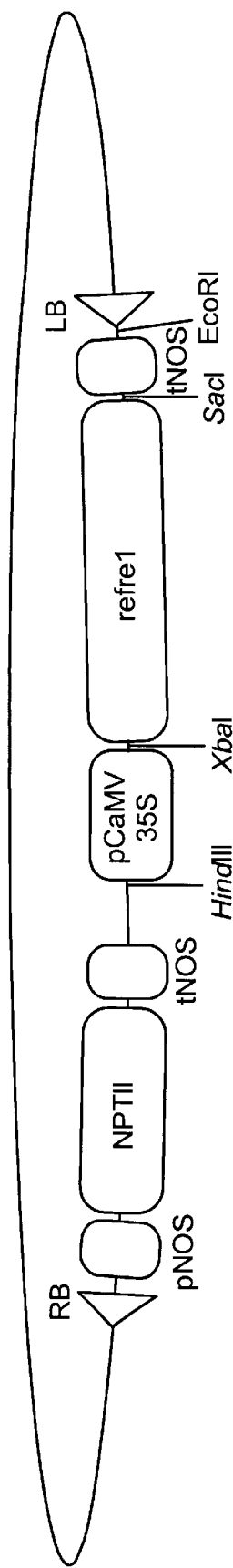
FIG. 11: Structure of binary vector pRF1.

Specifically, a fragment of restriction enzymes, XbaI and SacI, in refre1, which was cloned with pT7Blue(R) vector by the above method, was exchanged with ORF of β-glucuronidase in the binary vector pBI121 (TOYOBO Co. Ltd.) to prepare binary vector pRF1. The structure of the binary vector pRF1 is shown in FIG. 11.

The thus obtained binary vector pRF1 was transformed into *E. coli*, and *E. coli* which is bearing helper plasmid pRK2013, were shake cultured at 37° C. for overnight. On the other hand, *Agrobacterium tumefaciens* C58 was shake cultured in LB liquid culture medium 1 ml containing proper antibiotic at 26° C. for 2 nights. Each 100 μl thereof was mixed on LB plate without containing antibiotic, cultured at 26° C. for 2 nights, then surface of the plate was scraped by using platinum spatula, and cultured on the selection plate [LB plate containing 100 μg/μl rifampicin (Rf) and 25 μg/μl kanamycin (Km)] at 26° C. for 2 nights to form single colony.

The single colony was shake cultured in LB (Km and Rf) liquid medium 4 ml at 26° C. for 2 nights. Plasmid was extracted, and restriction enzyme treated cleavage pattern of the plasmid indicated existence of pRF1.

Plant to be transformed was prepared as follows.

Two or three young leaves, size about 8 cm, of wild type tobacco were cut, and were sterilized in a petri dish, filled with sterilized solution (hypochlorous acid 10% and Tween 20, 0.1%), with stirring for 15 minutes. After rinsing three times with sterilized water, the leaves were cut off in 8 mm squares. To the leaves in a petri dish was added the cultured liquid 3 ml of the binary vector bearing *Agrobacterium tumefaciens* C58, which was cultured 26° C. for 2 nights. After 1 minute, the liquid was rapidly removed by using Pasteur pipette, and residual liquid was removed off on the autoclaved filter paper.

Fragments of leaves were put on a culture medium, added with benzyl adenine and naphthaleneacetic acid to the MS medium, and cultured under light condition at 25° C. for 3 days. Thereafter, the fragments of leaves were transferred to the medium added with CLAFORAN, and cultured for 1 week further were transferred to the medium added with CLAFORAN and kanamycin, then inoculated in every 2 weeks. When calli were induced and shoots were formed, the shoots were cut off with scalpel and were transferred to the MS medium added with kanamycin.

Shoots with roots were transplanted to the vermiculite and the plants were raised with supplying hyponex (Hyponex Japan Co. Ltd.) to obtain the transgenic plants.

Figure 12:
FIG. 12: A photograph showing growth of transgenic plant of the present invention.
Figure 13:
FIG. 13: A photograph showing anthesis of transgenic plant of the present invention.

Sixty-eight transgenic plants having kanamycin resistance could be obtained as a result of transformation. Example of photograph of the grown plant is shown in FIG. 12 and the photograph of plant with flower is shown in FIG. 13.

Among them, 5 individual plants were treated with genomic Southern hybridization. Result is shown in FIG. 14.

In the genomic Southern hybridization, extraction of genomic DNA from the transgenic tobacco was performed according to the description in "Plant Cell Technology Series 2, Protocol for PCR Experiments of Plants" (Shujun-Sha) [Ref. (2)]. The obtained genomic DNA was digested by restriction enzymes EcoRI and HindIII and the hybridization was performed by using a probe, which was prepared with full length fragment of refre1 as a template ([α-32P]-dATP was used).

Figure 14:
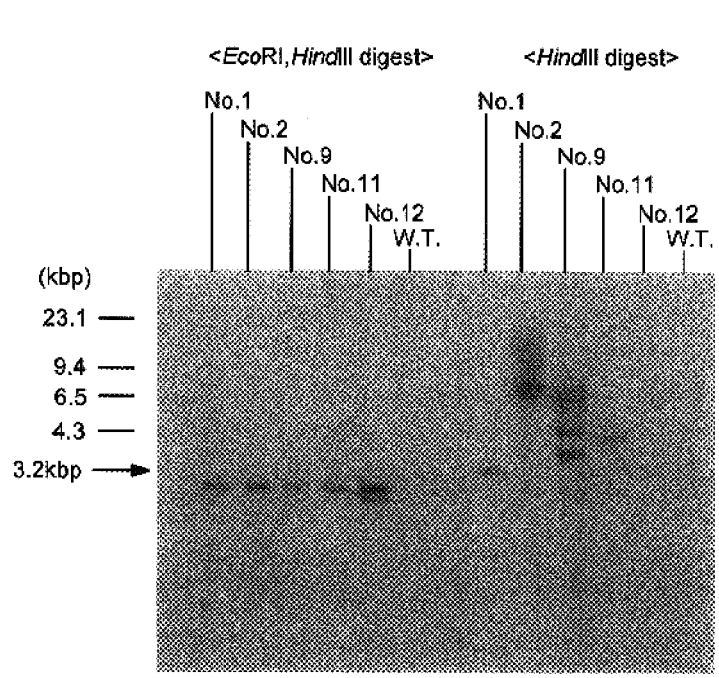
FIG. 14: Result of Southern hybridization of the transformant using refre1 as a probe.

In the genomic Southern hybridization shown in FIG. 14, amounts of DNA were arranged at the time of restriction enzyme treatment, but deviation was observed due to treating with ethanol after restriction enzyme treatment. Consequently, darkness of bands detected is not always reflecting the copy numbers of the introduced gene.

In digestion with restriction enzymes, EcoRI and HindIII, band, size 3.2 kb, which was expected in all individuals, was observed. However, in the individual No. 12, a band with slightly smaller than 3.2 kb was detected. According to this result, 1 copy of refre1 in No. 1 and No. 11, 3 or 4 copies in No. 2 and 4 copies in No. 9 were thought to exist.

In the digestion by HindIII on No. 12, band could not be detected due to loading failure on the gel.

As a result of the above genomic Southern hybridization analysis, the refre1 gene was found to be introduced into the selected five individuals.

When the sequence is cleaved by restriction enzymes EcoRI and HindIII, a sequence from promoter to terminator is cleaved, and the introduced refre1 gene is transcribed to mRNA under regulation of CaMV35S promoter. In the EcoRI and HindIII digestion of No. 12, a reason for detecting a band slightly smaller than 3.2 kb might be due to the fact that one of the introduced construction was cleaved before integration in the plant genom, and was inserted into the position close to EcoRI or HindIII site in the plant genom.

Next, in the transformed tobacco No. 1 and No. 2, in which the introduced refre1 gene was confirmed by the genomic Southern hybridization hereinbefore, formation of full length mRNA was confirmed by Northern analysis.

In the Northern analysis, a method of blotting was performed, for example, according to the conventional method described in "Cloning and Sequencing" (Noson-Bunka-Sha) [Ref. (1)], and the method in hybridization was performed according to the method as described in Southern analysis hereinbefore.

A result of Northern hybridization is shown in FIG. 15. In FIG. 15, no band is detected in the lane of wild type (W.T.). In lanes of No. 1 and No. 2, major bands with a size of 2.5 kb are detected and several bands smaller than that are detected.

In Northern analysis, formation of the full length mRNA as a result of introducing refre1 of the present invention could be confirmed. In the present analysis, fundamentally although total RNA should be extracted from the root, in which mRNA is expected to be expressed, in this experiment, if the root is cut, then the plant of the subsequent generation can not be obtained, consequently the extraction has to perform from leaves. Since CaMV35S as a promoter is used and refre1 gene is expressed in the whole parts of plant, even in the analysis performed by extraction of total RNA from leaves, it is confirmed that the transcription can be performed in leaves and roots of plants and site of addition of poly(A) is not changed.

As a result of Northern hybridization, since the transcriptional product of 2.5 kb was confirmed in the tobacco, to which rebel was introduced, poly(A) addition might occur by NOS terminator. Full length mRNA was also found in the tobacco, to which refre1 was introduced.

A band smaller than the length of 2.5 kb as seen in FIG. 15 is detected at the position corresponding to rRNA as compared with that of photograph after electrophoresis. Although it was thought to be a nonspecific absorption of probe in rRNA, since it was not hybridized with wild type RNA, it is surely hybridized with transcriptional product of refre1. There may be possibly produced the shorter mRNA than the full length mRNA in the refre1. However, since it is detected as the same length with rRNA, it may be thought that, in the electrophoresis of RNA, mRNA of refre1 may be dragged by rRNA, which exists in large amount. This reason may be clarified by Northern hybridization with purified poly(A)+RNA, however as obviously shown in FIG. 15, most of mRNA is full length mRNA and there is no reason to trace and clarify such the reason.

In order to perform Northern hybridization, RNA of the transformant of No. 1, which was found as one copy, and that of the transformants of No. 2, which were found as 3 or 4 copies, were electrophoresed, it was found that the bands of No. 2 were dark colored depending on copy numbers of refre1 gene.

Further, among the obtained transformed 68 plants of tobacco (selected by kanamycin), constant ferric-chelate reductase in root was confirmed in 6 plants.

For detection of reductase activity, a property of red color formation of the complex of bathophenanthroline disulfonic acid (BPDS), which is a strong chelater for Fe(II), with Fe(II) was applied. After removal of vermiculite from transformant and wild type tobacco, roots were laid on the gel containing BPDS with shield light using aluminum foil and stood at 27° C. for 24 hours. Reduction of Fe(III) was confirmed by coloring in the rhizosphere of the transformant.

Photographs confirming reductase activity are shown in FIG. 16 and FIG. 17. In photographs of FIG. 16 and FIG. 17, red coloring is observed in the transformant of the right photographs as shown with black color.

As shown, ferric-chelate reductase was detected in all of 6 plants (selected by kanamycin), which were used for confirmation of ferric-chelate reductase activity in roots. In order to demonstrate difference between the transformed tobacco and wild type tobacco, reaction time of reductase was set for long time as 24 hours, but the difference was observed at about 1 hour of the reaction time. In all of 6 plants used in the transformation experiments, the leaves, which were put on the gel for detecting activity, showed tendency of crinkle as compared with the condition of wild type leaves. This may be due to involvement in the mechanism of the introduced refre1 gene expression in the leaves. Though not so many times of activity tests were performed because of this phenomenon, it is clear that refre1 gene is expressed as a result of transcription and translation in the root under regulation of CaMV35S promoter.

As explained in the above, we have created novel tobacco which could express yeast ferric-chelate reductase FRE1 in the higher plant tobacco.

Reasons for not obtaining full length transcription product of different organism gene may be due to two possibilities including splicing a part of mRNA as an intron, and adding poly(A) within the coding region.

The present invention provides a method for designing base sequence for obtaining full length transcriptional product by transferring gene of different species in the higher plant. In the method of the present invention, in order to avoid addition of poly(A) in the coding region, it was found that it is necessary to design the sequence consisting of continued base sequence of 8 bases or more without containing sequence consisting of only G or T, and to design the sequence without containing not only a if sequence of AATAAA but also a sequence, in which any one of bases thereof is replaced by another base (i.e. NATAAA, ANTAAA, AANAAA, AATNAA, AATANA, or AATAAN).

It was also found that to design the sequence, in which G and C contents should be constantly distributed in the full region, is important.

Further, in the concrete explanation of the present invention hereinbefore, since CaMV35S was used as a promoter, ferric-chelate reductase was expressed in the transformed tobacco of the whole plant. As shown, locally expressing gene can be expressed in the systemic plant as a result of combining with the promoter. On the contrary, the expressing gene in the systemic plant can be expressed in the local region by using combination with preferable promoter.

A mechanism of absorption by reduction of Fe(III) is specific to iron acquiring mechanism in the monocots and dicots except for grass, and also the grass may absorb iron by reducing Fe(III) to Fe(II) under the condition of sufficient iron. As a result of ligating the ferric-chelate reductase gene refre1 of the present invention with a promoter, which is specifically active in the root under iron deficient condition, novel grass, in which iron absorption mechanism (I) and absorption mechanism (II) under the condition of iron deficiency can be functioned, may able to be created.

References in the present invention are listed hereinbelow.

(1) Cloning and Sequence (1989), Noson-Bunka-Sha
(2) Protocol of PCR Experiments for Plants (1995), Shujun-Sha
(3) Biological Experiments, Illustrated Fundamentals of Genetic Analysis (1995), Shujun-Sha
(4) Labolatory Manual, Functional Analysis of Plant Genes (1992), Maruzen
(5) Askwith, C., et al., Cell 76: 403–410 (1994)
(6) Brown, J. C., et al., Soil Sci. 91: 127–132 (1961)
(7) Chaney, R. L., et al., Plant Physiol. 50: 208–213 (1972)
(8) Dancis, A., et al., Mol. Cell. Biol. 10: 2293–2301 (1990)
(9) Dancis, A., et al., Proc. Natl. Acad. Sci. USA 89: 3869–3873 (1992)
(10) Dix, D. R., et al., J. Biol. Chem. 269: 26092–26099 (1994)
(11) Dix, D., et al., J. Biol. Chem. 272: 11770–11777
(12) Eide, D., et al., Proc. Natl. Acad. Sci. USA 93: 5624–5628 (1996)
(13) Fujimoto, H., et al., Bio/Technology 11: 1151–1155 (1993)
(14) Gallie, D. R., et al., Plant Cell 9: 667–673 (1997)
(15) Georgatsou, E., et al., Mol. Cell. Biol. 14: 3065–3073
(16) Guo, Z., et al., Biochem. Sci. 21: 477–481 (1996)
(17) Hassett, R., et al., J. Biol. Chem. 270: 128–134 (1995)
(18) Hether, N. H., et al., J. Plant Nutr. 7: 667–676 (1984)
(19) Hincha, D. K., et al., Plant Physiol. 147: 604–610 (1996)
(20) Kozak, M., J. Cell Biol. 108: 229–241 (1989)
(21) Lin, S. J., et al., J. Biol. Chem. 272: 9215–9220 (1997)
(22) Marschner, H., et al., J. Plant Nutr. 9: 695–713 (1986)
(23) Mewes, H. W., et al., Nature 387: 7–8 (1997)
(24) Mori, S., (1994), Biochemistry of metal micronutrients in the rizosphere. (Eds. Monthey, J. A., Crowley, D. E., Luster, D. G., Lewis Publishers), pp225–249
(25) Naito, S., et al., Plant Mol. Biol. 11: 109–124 (1988)
(26) Nakanishi, H., et al., Plant Cell Physiol. 34: 401–410 (1933)
(27) Nayak, P., et al., Proc. Natl. Acad. Sci. USA 94: 2111–2116 (1997)
(28) Ohme-Takagi, M., et al., Proc. Natl. Acad. Sci. USA 90: 11811–11815 (1993)
(29) Okumura, N., et al., J. Plant Nutr. 15: 2157–2172 (1992)
(30) Okumura, N., et al., Plant Mol. Biol. 25: 705–719 (1994)
(31) Olsen, R. A, et al., J. Plant Nutr. 2: 629660 (1980)
(32) Perlak, F. J., et al., Proc. Natl. Acad. Sci. USA 88: 3324–3328 (1991)
(33) Stearman, R., et al., Science 271: 1552–1557 (1996)
(34) Takagi, S., Soil Sci. Plant Nutr. 22: 423–433 (1976)
(35) Takagi, S., et al., J. Plant Nutr. 7: 469–477 (1984)
(36) Whiteley, H. R., et al., Annu. Rev. Microbiol. 40: 549–576 (1986)
(37) Wu, L., et al., Plant J. 8: 323–329 (1995)
(38) Yuan, D. S., et al., Proc. Natl. Acad. Sci. USA 92: 2632–2636 (1995)

EXAMPLES

The present invention will be explained in detail hereinbelow in examples, but is not construed as limiting within these examples.

In the examples hereinbelow, fundamental gene manipulation is performed according to the description of "Cloning and Sequencing" (Noson-Bunka-Sha) and analysis of base sequence of gene is performed by using DNASIS (made by Hitachi Corp.).

Example 1

Extraction of Total RNA from FRE1 Introduced Transgenic Tobacco

Extraction of total RNA from FRE1 introduced transgenic tobacco was performed according to a method described in the reference (Naito et al., 1988).

Leaves 2 g of FRE1 introduced transgenic tobacco were put in the mortar, and liquid nitrogen was added thereto, then leaves were completely mashed. Three fold amounts of buffer for extraction and equal amount of phenol/chloroform (1:1) were added to the debris and suspended, then centrifuged at 8000 rpm for 15 minutes, and extracted with chloroform once. Ethanol precipitation was conducted at −80° C. for 30 minutes, and centrifuged at 4° C. for 30 minutes. Precipitate was washed with 70% ethanol and dried in vacuum. The precipitate was dissolved in DEPC treated water 1 ml, centrifuged at 13500 rpm for 3 minutes, and the supernatant was transferred to a new tube, further 10 M LiCl, ¼ volume, was added and allowed to stand on ice for 2 hours. The mixture was centrifuged at 12000 rpm at 4° C. for 10 minutes, then the precipitate was washed with 70% ethanol and dried in vacuo. The dried product was dissolved in DEPC treated water 50 μl.

Reagent buffer for extraction

1M Tris HCl pH 9.0

1% SDS (β-mercaptoethanol 120 μl was added to 6 ml of buffer before use)

Example 2

Purification of poly(A)+RNA and Synthesis of cDNA)

Poly(A)+RNA was purified from total RNA 100 μg obtained in example 1 by applying with Dynabeads Oligo (dT) 25 (DYNAL Inc.). This poly(A)+RNA was treated with reverse transcription reaction by M-MLV reverse transcriptase (TOYOBO Co. Ltd.) at 37° C. for 1 hour using the following hybrid primer to obtain cDNA.

Hybrid primer (dT$^{17}$ adapter primer): 5'-GACTCGAGTCGACATCGATTTTTTTTTTTTTTTTT-3' (SEQ ID NO: 35)

Example 3

RT-PCR and Confirmation of Base Sequence

PCR was conducted with the primer specific to hybrid primer and the 5' primer of FRE1 using cDNA obtained in example 2 as a template.

Reaction product of PCR was electrophoresed with 0.8% agarose gel, and the obtained band was cloned to pT7Blue (R) vector (Takara Corp.). Colony was shake cultured in LB medium for overnight, extracted the plasmid by alkaline-SDS method, and the base sequence of 7 clones, to which the insertion was confirmed by restriction enzyme treatment, was determined by using Bca BEST DNA polymerase ("Biotechnology Experiments Illustrated, Fundamentals of gene analysis") (Shujun-Sha).

Primer specific to hybrid primer: 5'-GACTCGAGTCGACATCG-3' (SEQ ID NO: 3)

5' primer of FRE1: 5'-ACACTTATTAGCACTTCATGTATT-3' (SEQ ID NO: 4)

Reaction condition for PCR:

(1) 95° C. for 5 minutes;

(2) 95° C. for 40 seconds;

(3) 55° C. for 30 seconds;

(4) 72° C. for 1 minute;

(5) 72° C. for 10 minutes; and (6) 4° C.

In the above procedures, (2), (3) and (4) were repeated 40 times.

As a result, in the transgenic tobacco transformed with FRE1, poly(A) was attached at the position as shown in FIG. 3, in the transcribed mRNA from FRE1 gene.

Attached points of poly(A) were not uniform, and several length of mRNA was observed. A sequence, which might be recognized as poly(A) signal at the upstream of poly(A) site, was indicated as putative poly(A) signal.

Example 4

Production of Each Segment by PCR)

Each segment was prepared by PCR as illustrated in FIG. 5. The super Taq (Sawady Inc.) was used as Taq polymerase. Composition of PCR reaction is as follows.

PCR reaction solution in the first step:

| | |
|---|---|
| 10 x buffer | 10 μl |
| 2 mM dNTP mixture | 10 μl |
| 20 μM primer (−3) | 5 μl |
| 20 μM primer (−4) | 5 μl |

PCR reaction solution in the second step:

| | |
|---|---|
| PCR reaction solution in the first step | 1 μl |
| 10 x buffer | 1 μl |
| 2 mM dNTP mixture | 10 μl |
| 20 μM primer (−2) | 5 μl |
| 20 μM primer (−5) | 5 μl |
| distilled water to total volume | 99.5 μl |

PCR reaction solution in the third step:

| | |
|---|---|
| PCR reaction solution in the second step | 1 μl |
| 10 x buffer | 10 μl |
| 2 mM dNTP mixture | 10 μl |
| 20 μM primer (−1) | 5 μl |
| 20 μM primer (−6) | 5 μl |
| distilled water to total volume | 99.5 μl |

Reaction conditions for PCR:

(1) 95° C. for 5 minutes;

(2) add Taq 0.5 μl;

(3) 95° C. for 40 seconds;

(4) 45° C. for 1 minute;

(5) 72° C. for 1 minute;

(6) 94° C. for 40 seconds;

(7) 60° C. for 30 seconds;

(8) 72° C. for 1 minute;

(9) 72° C. for 10 minutes;

(10) 4° C.

The above procedures of (3), (4) and (5) were repeated 5 times, and the procedures of (6), (7) and (8)) were repeated 20 times, respectively.

Example 5

Cloning and Confirmation of Base Sequence

After electrophoresis of PCR reaction solution in the third step in example 4 with 0.8% agarose gel, a band, which had expected length (417–436 bp), was cleaved and purified, then was cloned into the plasmid pT7Blue (R) vector (Takara Inc.). The base sequence of the thus obtained clone was confirmed and the exact base sequence was selected using SHIMADZU luminescent DNA sequencer DSQ-1000L.

After obtaining segment of each exact sequence, full length of refre1 was prepared as shown in FIG. 8 by applying with restriction enzyme sites. A direction of insertion of the segment B and E was essential for preparing the full length. As for the other segments, the sequence containing exact base sequence was used without relation to the direction of insertion.

Full length of base sequence of the synthesized refre1 is shown in sequence listing SEQ ID NO: 1 and FIG. 9.

Example 6

Introduction of refre1 into Tobacco)

A gene refre1 synthesized in example 5 was introduced into tobacco (*Nicotiana tabacum* L. var. SRI). As a result of transformation, 68 individual plants resistant to kanamycin were generated. Genomic Southern hybridization was performed in order to confirm introduction of refre1, an objective gene, in the generated plant and copying number thereof. As a result, existence of one to several copies of refre1 gene was confirmed.

A method from gene introduce into plant cells to generation of plant was performed according to description in "Laboratory Manual for Functional Analysis of Plant Genes" (Maruzen).

(1) Preparation of Binary Vector pRF1 for Transformation

XbaI and SacI fragments of refre1, which were cloned in pT7Blue (R) vector, were exchanged with ORF of β-glucronidase of binary vector pBI121 to prepare a binary vector pRF1. A structure of the binary vector pRF1 is shown in FIG. 11.

(2) Transfer of Binary Vector pRF1 into *Agrobacterium*

Agrobacterium tumefaciensC58 was shake cultured at 26° C. for 2 nights in LB liquid medium 1 ml containing suitable antibiotic, and *E. coli* having pRF1 and *E. coli* having helper plasmid pRK2013 were shake cultured at 37° C. for one night in LB liquid medium 1 ml containing suitable antibiotic. Each 100 µl was mixed on the LB plate without containing antibiotics. After the mixture was cultured at 26° C. for 2 nights, plate surface was scraped out the plate using platinum loop and incubated to form single colony on the selection plate [LB plate containing 100 µg/µl rifampicin (Rf) and 25 µg/µl kanamycin (Km)] (at 26° C. for 2 nights).

The thus obtained single colony was shake cultured in LB (Km and Rf) liquid medium 4 ml at 26° C. for 2 nights, and the plasmid was extracted by alkaline-SDS method, then existence of pRF1 was confirmed by observing cleavage patterns by restriction enzymes.

(3) Infection of *Agrobacterium* to Tobacco and Regeneration of Plant

Two or three young leaves of tobacco (*Nicotiana tabacum* L. var. SRI), size about 8 cm, were cut, put them into the petri dish filled with sterilized water (hypochlorous acid 10% and Tween 20, 0.1%), and sterilized with stirring for 15 minutes. The leaves were rinsed with sterilized water for 3 times, and were cut in 8 mm square using scalpel. Cultured liquid of *Agrobacterium* 3 ml having binary vector pRF1 cultured at 26° C. for 2 nights was added to fragments of leaves in the petri dish.

After one minute, the liquid was immediately removed off by using Pasture pipette and the residual liquid was removed off using autoclaved sterilized filter paper. The leaves were put on the MS medium (II) hereinbelow and cultured at 25° C. for 3 days under lighting condition. Thereafter fragments of leaves were transferred to MS medium (III) and cultured for 1 week, then transferred to the MS medium (IV) and subcultured in every 2 weeks. When calli were induced and shoots were formed, the shoots were cut using scalpel and transferred to the MS medium (V). The shoots with roots were inoculated to vermiculite, and raised with supplying hyponex (Hyponex Japan Co., Ltd) to obtain the regenerated plant.

The compositions of MS medium for tobacco used in the experiments hereinbefore are as follows.

| Major elements (g/l) | |
| --- | --- |
| $NH_4NO_3$ | 1.65 |
| $KNO_8$ | 1.9 |
| $CaCl_2.2H_2O$ | 0.44 |
| $MgSO_4.7H_2O$ | 0.44 |
| $KH_2PO_4$ | 0.17 |
| Minor elements (mg/l) | |
| $H_3BO_4$ | 6.2 |
| $MnSO_4.4H_2O$ | 22.3 |
| $ZnSO_4.7H_2O$ | 8.6 |
| KI | 0.83 |
| $Na_2MoO_4.2H_2O$ | 0.25 |
| $CuSO_4.5H_2O$ | 0.025 |
| $CoCl_2.6H_2O$ | 0.025 |
| Fe(III)Na-EDTA | 0.042 mg/l |
| myo-inositol | 100 mg/l |
| thiamine | 5 mg/l |
| sucrose | 30 g/l |
| geranylated g | 2 g/l |

MS medium (I) was prepared by the composition hereinbefore. The other MS media were prepared by adding the following phytohormone and/or antibiotics to the MS medium (I).

| Phytohormone | |
| --- | --- |
| benzyladenine (BA) | 1.0 mg/l |
| naphthaleneacetic acid (NAA) | 0.1 mg/l |
| Antibiotics | |
| kanamycin | 100 mg/l |
| claforan | 200 mg/l |

MS medium (I) MS medium (I)+BA+NAA

MS medium (III) MS medium (I)+BA+NAA+claforan

MS medium (IV) MS medium (I)+BA+NAA+claforan +kanamycin

MS medium (V) MS medium (I)+kanamycin

Example 7

Southern Analysis (1) Extraction of Genomic DNA from Tobacco

Extraction of genomic DNA from tobacco was performed according to the method described in "Plant Cell Engineering Series: Protocol for PCR Experiments in Plant" (Shujun-Sha).

Leaves 0.1–0.2 g were put in the mortar, and liquid nitrogen was added thereto, then leaves were completely mashed. The crushed leaves were put into the Eppendorf tube, and 2% CTAB solution 300 µl was added and mixed, then treated at 65° C. for 30 minutes. Equal amount of chloroform and isoamyl alcohol (24:1) was added and mixed for 5 minutes.

The mixture was centrifuged at 12000 rpm for 15 minutes, and the upper layer was transferred to the new tube, then chloroform-isoamyl alcohol extraction was repeated once again, and the upper layer was transferred to the new tube. 1–1.5 volume of 1% CTAB solution was added, mixed, allowed standing at room temperature for 1 hour, and centrifuged at 8000 rpm for 10 minutes. The upper layer was discarded and 1M CsCl 400 µl was added to the residue, and heated at 65° C. until complete dissolving the precipitate. 100% ethanol 800 μl was added thereto, mixed, allowed to standing at −20° C. for 20 minutes, then centrifuged at 12000 rpm for 5 minutes. The upper layer was discarded, and the residue was washed with 70% ethanol, dried in vacuum and dissolved in TE buffer 30 μl.

| Reagents | |
|---|---|
| 2% CTAB Solution | |
| Tris-HCl (pH 8.0) | 100 mM |
| EDTA (pH 8.0) | 20 mM |
| NaCl | 1.4 M |
| CTAB (cetyltrimethylammonium bromide) | 2% |
| 1% CTAB solution | |
| Tris-HCl (pH 8.0) | 50 mM |
| EDTA (pH 8.0) | 20 mM |
| CTAB | 1% |

(2) Cleavage of Genomic DNA by Restriction Enzyme and Electrophoresis

Restriction enzyme treatments were performed by digestion using EcoRI and HindIII, by which sequence from pCaMV35S to tNOS was cleaved, and by digestion using only HindIII, by which sequence of upstream of pCaMV35S was cleaved.

Genomic DNA 10 μg with the reaction volume 100 μl was treated by restriction enzyme for overnight, precipitated by adding ethanol and dissolved the precipitate in TE buffer 20 μl. To the solution was added the loading buffer 2 μl, and the solution was electrophoresed with 0.8% agarose gel at 60V for 5 hours. After completion of electrophoresis, gel was stained with ethidium bromide and photographed on the UV transluminater with the scale.

(3) Blotting and Hybridization

Gel after photographing was washed with distilled water, and was shaken in 0.2 N HCl for 10 minutes. A method of blotting was performed according to the description in "Cloning and Sequencing" (Noson-Bunka-Sha). The gel was transferred to nylon membrane (New Hybond-N+ Amersham) with 0.4 N NaOH, and the membrane washed with 2×SSPE for 5 minutes, and dried at room temperature for 3 hours. A method of hybridization was referred with "Biotechnology Experiments Illustrated, Fundamentals of Gene Analysis" (Shujun-Sha) The membrane was treated for prehybridization with prehybridization buffer 30 ml, which was previously warmed at 65° C., for 1 hour at 65° C., and the hybridization buffer was exchanged (25 ml). Probe was added and hybridization was performed at 65° C. for 12 hours. The membrane was washed with washing solution, which was previously warmed at 65° C., twice at 65° C. for 10 minutes, and was washed once with high stringent washing solution at 65° C. for 10 minutes. The membrane was wrapped with Saran wrap, exposed on imaging plate for 24 hours, and result was confirmed by image analyzer (Fuji Photo Film Co. Ltd.).

| Reagents | |
|---|---|
| 20 × SSPE | |
| NaCl | 3 M |
| NaH$_2$PO$_4$ | 0.2 M |
| EDTA | 1 mM |
| 1M Church phosphate buffer | |

NaHPO$_4$ 0.5 mol was added to distilled water about 800 ml, adjusted pH to 7.2 by H$_3$PO$_4$, then filled up to 1 liter by adding distilled water, and autoclaved.

| Hybridization buffer | |
|---|---|
| Church phosphate buffer | 0.5 M |
| EDTA | 1 mM |
| SDS (v/v) | 7% |

Denatured salmon sperm (1 mg/ml) 1/100 vol. was added before use.

| Washing solution | |
|---|---|
| Church phosphate buffer | 40 mM |
| SDS (v/v) | 1% |
| High stringent washing solution | |
| 0.2 × SSPE | |
| SDS (v/v) | 0.1% |

(4) Preparation of Probe

Probe was prepared by random primer DNA labeling kit ver. 2.0 (Takara Corp.) using full length refre1 as a template (proviso that [α-$^{32}$P]-dATP was used), and non-reacted [α-$^{32}$P]-dATP was removed using Probe Quant TM G-50 Micro Columns (Pharmacia, Biotech Inc.).

Result is shown in FIG. 14. The left side in FIG. 14 shows digestion using restriction enzymes EcoRI and HindIII, and the right side in FIG. 14 shows digestion using only HindIII. In FIG. 14, W.T. means wild type.

Example 8

Northern Analysis (1) Extraction of total RNA

Total RNA was extracted from leaves of the transgenic tobacco, to which refre1 gene was introduced, and leaves of the wilt type tobacco according to the same method as described in example 1.

(2) Electrophoresis of RNA

Electrophoresis vessel, gel receiver, comb and Erlenmeyer flask were treated previously with abSolve (RNase inhibitor, Du Pont Inc.). 20×MOPS 10 ml, agarose 2.4 g and sterilized distilled water 100 ml were poured into Erlenmeyer flask, and agarose was dissolved using microwave oven. Formaldehyde 10 ml was added to the gel which was cooled to about 50° C., and sterilized distilled water was added up to 200 ml, which was used when gelification occurred. 1×MOPS about 800 ml was added in the electrophoresis vessel, and added ethidium bromide 10 mg/ml thereto for use as electrophoresis buffer. RNA sample buffer 16 μl was added to the total RNA 10 μg, filled up to 20 μl with sterilized distilled water, and the mixture was warmed at 65° C. for 10 minutes, then allowed to standing for 5 minutes on ice, and was electrophoresed. Electrophoresis condition was that after electrophoresis was performed at 60 V for 1 hour, further electrophoresis was performed at 120

V for 2 hours.

| Reagents: | |
|---|---|
| 20 × MOPS | |
| MOPS | 0.4 M |
| NaOAc | 0.1 M |
| EDTA | 0.02 M |
| RNA sample buffer | |
| Formaldehyde | 1.6 ml |
| Formamide | 5.0 ml |
| 20 × MOPS | 0.5 ml |
| glycerol pigment solution | 1.6 ml |
| Total | 8.7 ml |
| Glycerol pigment solution | |
| glycerol | 5 ml |
| bromophenol blue | 1 mg |
| xylenecyanol | 1 mg |
| 0.5 M EDTA (pH 8.0) | 0.02 ml |

(3) Blotting and Hybridization

After electrophoresis, gel was set on UV illuminator and photographed with the scale. A method of blotting was followed according to the description in "Cloning and Sequencing" (Noson-Bunka-Sha). Namely, RNA was transferred from gel to nylon membrane (New Hybond-N, Amersham Inc.) with 20×SSPE. After 12 hours, the membrane was washed with 2×SSPE for 5 minutes, and dried at room temperature for 3 hours, then RNA was fixed on the membrane by irradiating with UV for 5 minutes.

A method of hybridization was performed as same as the case of Southern analysis.

Result is shown in FIG. 15. In FIG. 15, WT. indicates wild type. No band was detected in the lane of wild type (W.T.). In No. 1 and No. 2 lanes, major band was detected at the size of 2.5 kb, and several bands were detected in the lower position thereof.

Example 9

Confirmation of Ferric-Chelate Reductase

The transgenic tobacco, to which refre1 gene was introduced, and wild type tobacco were transplanted in vermiculite and raised with supplying hyponex. Ferric-chelate reductase activity was confirmed by using plants, about 5 cm –10 cm.

For confirmation of ferric-chelate reductase activity, red coloring generated by formation of complex with bathophenanthroline disulfonic acid (BPDS), which was strong chelating agent for Fe(II), and Fe(II) was applied. Agarose was added to assay buffer up to 0.4%, dissolved by using microwave oven, and cooled. 500 µM Fe(III)-EDTA, 1/100 vol., and 500 µM BPDS, 1/100 vol., were added to the slightly cooled gel, and stirred to put in the vessel, then waited for solidification. After removed off vermiculite from the transformant and wild type tobacco, roots were laid on the gel, and shielded from light and allowed to standing at 27° C. for 24 hours.

The similar experiment was performed using second generation of the was germinated from seeds of the regenerated plant. Reaction was set for 1 hour.

| Assay buffer | |
|---|---|
| CaSO$_4$ | 0.2 mM |
| MES buffer pH 5.5 | 5.0 mM |

Photographs showing confirmation of ferric-chelate reductase activity are shown in FIG. 16 and FIG. 17. Photograph showing confirmation of ferric-chelate reductase activity of the second generation plant is shown in FIG. 18. Reduction of Fe(III) was confirmed as a result of coloring of the transformant in the rhizosphere.

What is claimed is:

1. A nucleic acid having a modified base sequence of a ferric-chelate reductase gene FRE1 derived from *Saccharomyces cerevisiae*, wherein the sequence is modified by (A) and (B) without altering the amino acid sequence thereof, for eliminating the sequences relating to poly(A) addition, and for introducing said gene into a plant, wherein (A) and (B) are defined as follows:

(A) eliminating GT rich regions comprising 8 or more consecutive bases of G or T, and
   (B) eliminating sequences AATAAA, NATAAA, ANTAAA, AANAAA, AATNAA, AATANA, and AATAAN.

2. The DNA according to claim 1, wherein the DNA has a base sequence as set forth in SEQ ID NO: 1.

* * * * *